United States Patent
Levin

(10) Patent No.: US 11,918,307 B1
(45) Date of Patent: Mar. 5, 2024

(54) INTEGRATING APPLICATIONS IN A SURGEON CONSOLE USER INTERFACE OF A ROBOTIC SURGICAL SYSTEM

(71) Applicant: Verily Life Sciences LLC, South San Francisco, CA (US)

(72) Inventor: Michal Levin, Sunnyvale, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 583 days.

(21) Appl. No.: 16/949,619

(22) Filed: Nov. 6, 2020

Related U.S. Application Data

(60) Provisional application No. 62/935,771, filed on Nov. 15, 2019.

(51) Int. Cl.
| | | |
|---|---|---|
| *G06F 3/14* | (2006.01) | |
| *A61B 18/12* | (2006.01) | |
| *A61B 18/14* | (2006.01) | |
| *A61B 34/00* | (2016.01) | |
| *A61B 34/30* | (2016.01) | |
| *A61B 34/37* | (2016.01) | |
| *G05B 19/4155* | (2006.01) | |

(Continued)

(52) U.S. Cl.
CPC .......... *A61B 34/25* (2016.02); *A61B 18/1206* (2013.01); *A61B 18/1445* (2013.01);
(Continued)

(58) Field of Classification Search
CPC . A61B 34/25; A61B 18/1206; A61B 18/1445; A61B 34/30; A61B 34/37;
(Continued)

(56) References Cited

U.S. PATENT DOCUMENTS

| 8,398,541 B2 | 3/2013 | DiMaio et al. |
|---|---|---|
| 8,418,073 B2 | 4/2013 | Mohr et al. |

(Continued)

FOREIGN PATENT DOCUMENTS

| CA | 3035251 A1 * | 3/2018 | ............. A47B 21/02 |
|---|---|---|---|
| CN | 101291635 A * | 10/2008 | ......... A61B 1/00193 |

(Continued)

OTHER PUBLICATIONS

Huang Yanpei, Development of an Intuitive Foot-Machine Interface for Robotic Surgery, retrieved from—https://arxiv.org/ftp/arxiv/papers/1905/1905.11191.pdf, 2018, 99 pages (Year: 2018).*

(Continued)

*Primary Examiner* — Yongjia Pan
(74) *Attorney, Agent, or Firm* — Kilpatrick Townsend & Stockton LLP

(57) ABSTRACT

One example method for improving the efficiency of robotic surgical procedures by integrating applications into the surgeon console user interface is presented. The method includes generating and displaying a first graphical user interface at a surgeon console associated with a robotic surgical device during a robotic surgical procedure, and detecting a combination of user actions through control devices of the surgeon console. The method further includes responsive to detecting the combination of the user actions, causing surgical tools of the robotic surgical device to be locked and generating and displaying a second graphical user interface at the surgeon console which includes user interfaces of applications and is configured to be interactive through the control devices. The method further includes detecting a user action to exit the application mode, causing the surgical tools to be unlocked, and updating and displaying the first graphical user interface at the surgeon console.

19 Claims, 19 Drawing Sheets

(51) Int. Cl.
*G16H 20/40* (2018.01)
*G16H 40/40* (2018.01)
*G16H 40/63* (2018.01)
*H04N 7/18* (2006.01)
*A61B 17/00* (2006.01)

(52) U.S. Cl.
CPC .............. *A61B 34/30* (2016.02); *A61B 34/37* (2016.02); *A61B 34/74* (2016.02); *G05B 19/4155* (2013.01); *G06F 3/14* (2013.01); *G16H 20/40* (2018.01); *G16H 40/40* (2018.01); *G16H 40/63* (2018.01); *H04N 7/185* (2013.01); *A61B 2017/00199* (2013.01); *A61B 2017/00225* (2013.01); *A61B 2017/00973* (2013.01); *A61B 2018/126* (2013.01); *A61B 2034/252* (2016.02); *A61B 2034/254* (2016.02); *A61B 2034/301* (2016.02); *A61B 2034/302* (2016.02); *A61B 2034/303* (2016.02); *A61B 2034/742* (2016.02); *G05B 2219/45123* (2013.01)

(58) Field of Classification Search
CPC .......... A61B 34/74; A61B 2017/00199; A61B 2017/00225; A61B 2017/00973; A61B 2018/126; A61B 2034/252; A61B 2034/254; A61B 2034/301; A61B 2034/302; A61B 2034/303; A61B 2034/742; G05B 19/4155; G05B 2219/45123; G06F 3/14; G16H 20/40; G16H 40/40; G16H 40/63; H04N 7/185
See application file for complete search history.

(56) References Cited

U.S. PATENT DOCUMENTS

| | | | |
|---|---|---|---|
| 9,283,054 B2 | 3/2016 | Morgan et al. | |
| 10,368,955 B2 * | 8/2019 | Cone | G05G 1/305 |
| 2004/0225282 A1 | 11/2004 | Ness | |
| 2009/0088775 A1 * | 4/2009 | Swarup | A61B 34/71 700/264 |
| 2009/0118714 A1 * | 5/2009 | Teodorescu | A61B 34/25 606/1 |
| 2010/0137880 A1 | 6/2010 | Nahum et al. | |
| 2010/0228264 A1 | 9/2010 | Robinson et al. | |
| 2014/0055489 A1 | 2/2014 | Itkowitz et al. | |
| 2014/0075479 A1 | 3/2014 | Soto et al. | |
| 2014/0081455 A1 | 3/2014 | Goldberg et al. | |
| 2014/0165000 A1 | 6/2014 | Fleizach et al. | |
| 2016/0092038 A1 | 3/2016 | Dyar et al. | |
| 2017/0129108 A1 * | 5/2017 | Diolaiti | A61B 34/76 |
| 2017/0202630 A1 | 7/2017 | Gerstner | |
| 2017/0360510 A1 | 12/2017 | Bischoff et al. | |
| 2018/0049828 A1 * | 2/2018 | Robinson | A61B 34/76 |
| 2019/0125182 A1 * | 5/2019 | Charles | A61F 2/16 |
| 2019/0133689 A1 * | 5/2019 | Johnson | G06F 3/011 |
| 2019/0183591 A1 * | 6/2019 | Johnson | G16H 20/40 |
| 2021/0145526 A1 | 5/2021 | Robinson et al. | |

FOREIGN PATENT DOCUMENTS

| | | | | |
|---|---|---|---|---|
| CN | 108806772 | | 11/2018 | |
| CN | 110013313 A | * | 7/2019 | ............ A61B 34/20 |
| WO | 2015126133 | | 8/2015 | |
| WO | 2017007929 | | 1/2017 | |
| WO | WO-2017220822 A1 | * | 12/2017 | ............ A61B 34/25 |
| WO | WO-2019117926 A1 | * | 6/2019 | ........... A61B 1/0005 |

OTHER PUBLICATIONS

U.S. Appl. No. 16/949,618, "Non-Final Office Action", dated Jun. 9, 2023, 17 pages.
U.S. Appl. No. 16/949,618, Corrected Notice of Allowability, dated Dec. 21, 2023.
U.S. Appl. No. 16/949,618, Notice of Allowance, dated Dec. 14, 2023.

\* cited by examiner

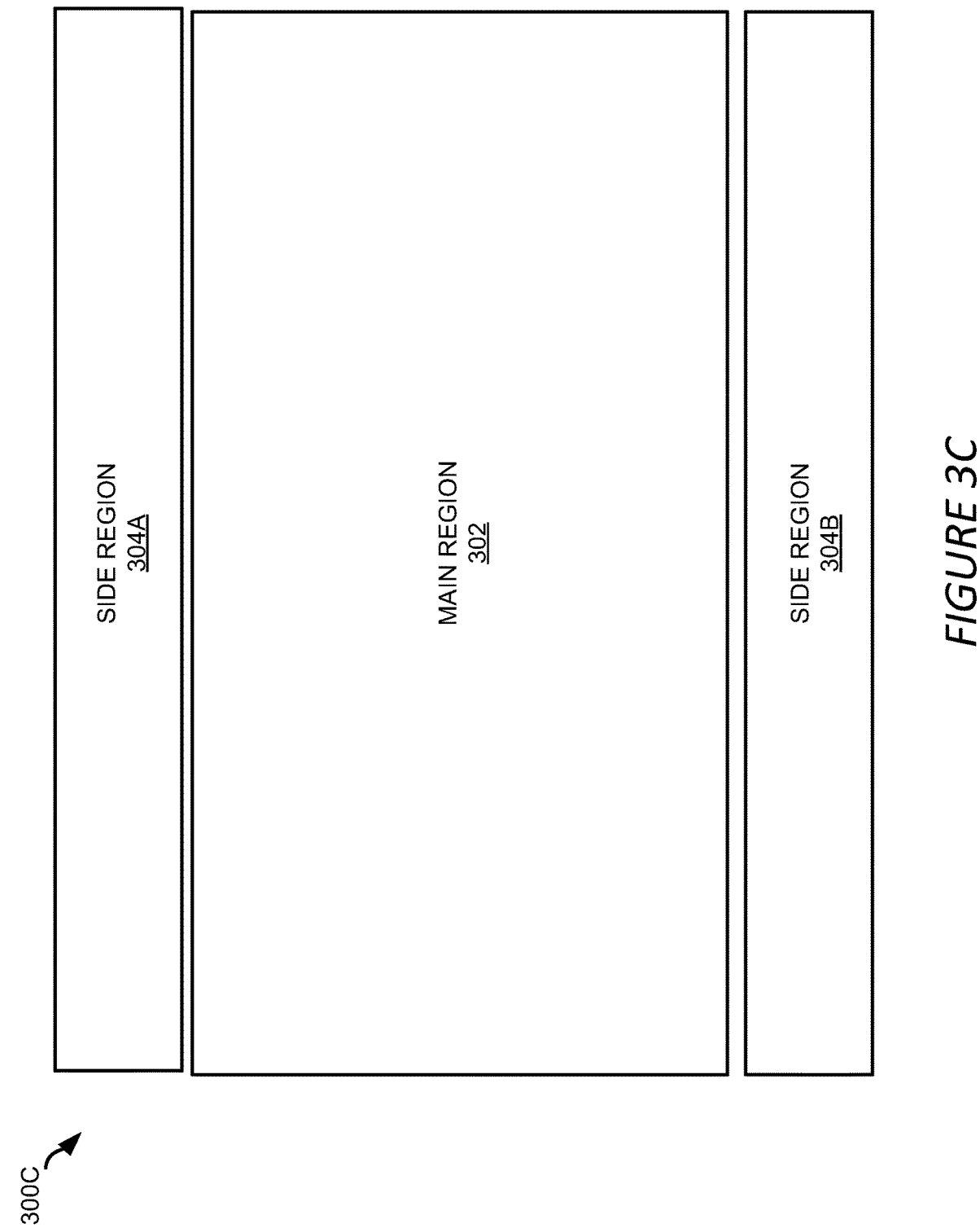

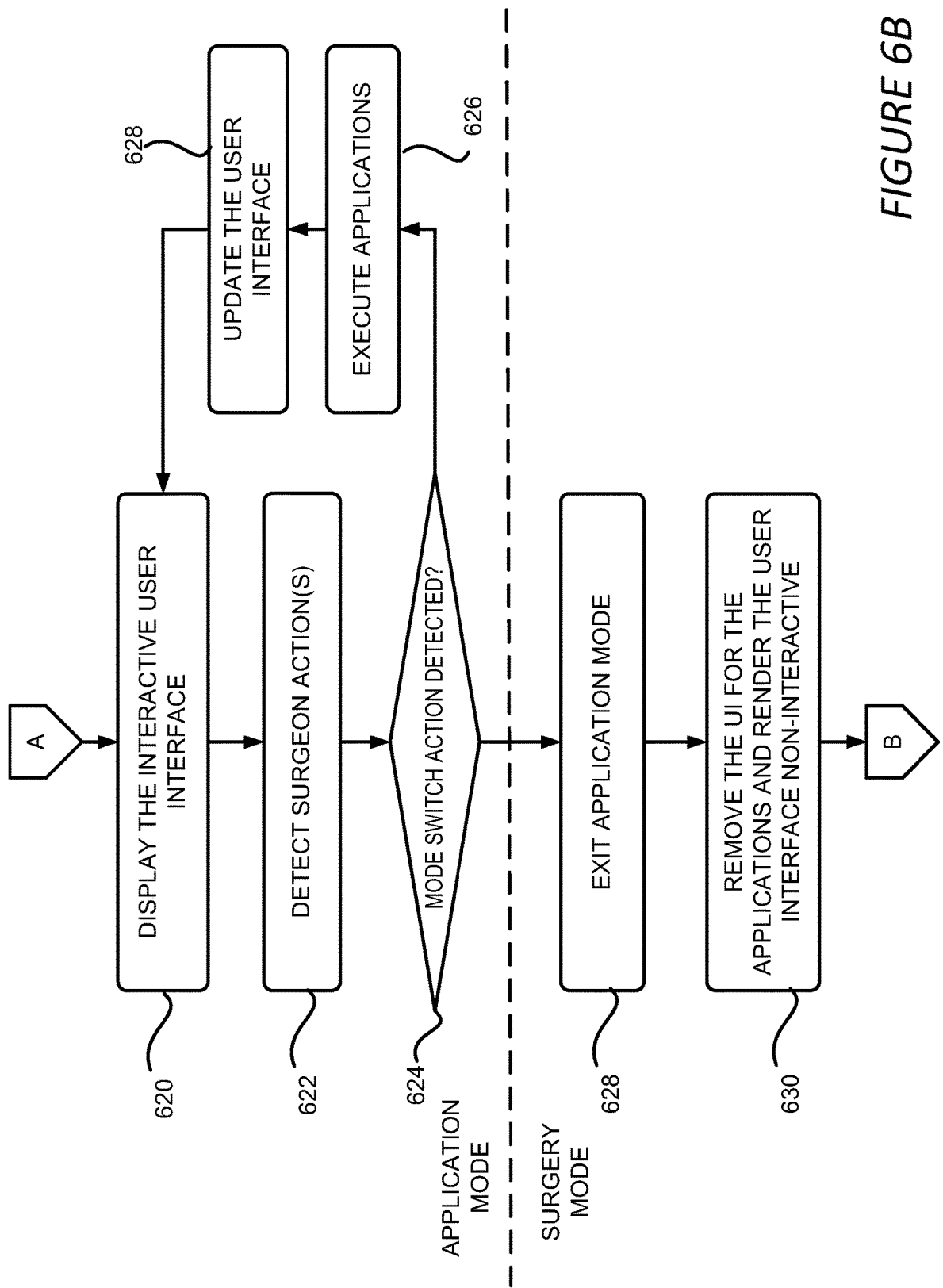

INTEGRATING APPLICATIONS IN A SURGEON CONSOLE USER INTERFACE OF A ROBOTIC SURGICAL SYSTEM

CROSS-REFERENCE TO RELATED APPLICATIONS

This application claims priority to U.S. Provisional Patent Application No. 62/935,771, filed Nov. 15, 2019, titled "Integrating Applications In A Surgeon Console User Interface Of A Robotic Surgical System," the entirety of which is hereby incorporated by reference.

FIELD

The present application generally relates to robotic surgery procedure, and more particularly relates to improving the efficiency of robotic surgery procedures by integrating interactive applications into surgeon console user interfaces.

BACKGROUND

Robotic surgeries are becoming increasingly popular because of their advantages over the traditional human-operated open surgeries. Surgical tools utilized in robotic surgeries have improved levels of dexterity over a human surgeon. These tools can provide the surgeon maximum range of motion and precision. In addition, high-definition cameras associated with the surgical tools can provide a better view of the operating site to the surgeon than human eyes can provide. Further, the small size of the robotic surgical tools allows the surgeries to be done in a minimally invasive manner thereby causing less trauma on the patient's body.

SUMMARY

Various examples are described for improving the efficiency of robotic surgical procedures by integrating applications into the surgeon console user interface. One example method includes generating and displaying a first graphical user interface at a surgeon console associated with a robotic surgical device during a robotic surgical procedure, wherein the robotic surgical device comprises a plurality of surgical tools, the surgeon console comprises a plurality of control devices configured to control the plurality of surgical tools to perform the robotic surgical procedure, the plurality of control devices comprise a clutch device configured to, when activated, cause the plurality of surgical tools locked, and the first graphical user interface is configured to display information related to the robotic surgical procedure and is non-interactive. The method further includes detecting a combination of user actions through the plurality of control devices, wherein the combination of user actions causes the surgeon console to operate in an application mode, and wherein the combination of user actions comprises activating the clutch device. In response to detecting the combination of the user actions, the method includes causing the plurality of surgical tools to be locked, and generating and displaying a second graphical user interface at the surgeon console, wherein the second graphical user interface comprises user interfaces of one or more applications and is configured to be interactive through one or more of the plurality of control devices. The method also includes detecting a user action to exit the application mode, wherein the user action to exit the application mode comprises at least releasing the clutch device. In response to detecting the user action to exit the application mode, the method includes causing the plurality of surgical tools to be unlocked, and updating and displaying the first graphical user interface at the surgeon console.

One example robotic surgical system includes a robotic surgical device configured to control a plurality of surgical tools to perform a robotic surgical procedure, a surgeon console configured to control the robotic surgical device. The surgeon console includes a display device and a plurality of control devices configured to control the plurality of surgical tools to perform the robotic surgical procedure. The plurality of control devices comprise a clutch device configured to, when activated, cause the plurality of surgical tools locked. The robotic surgical system further includes a control device in communication with the robotic surgical device and the surgeon console. The control device includes a processor and a non-transitory computer-readable medium having processor-executable instructions stored thereupon, which, when executed by the processor, cause the processor to generate and display a first graphical user interface on the display device of the surgeon console, the first graphical user interface configured to display information related to the robotic surgical procedure and is non-interactive, detect a combination of user actions through the plurality of control devices, wherein the combination of user actions causes the surgeon console to operate in an application mode, wherein the combination of user actions comprises activating the clutch device. In response to detecting the combination of the user actions, the instructions further causes the processor to cause the plurality of surgical tools to be locked and generate and display a second graphical user interface at the surgeon console. The second graphical user interface comprises user interfaces of one or more applications and is configured to be interactive through one or more of the plurality of control devices. The instructions further causes the processor to detect a user action to exit the application mode comprising at least releasing the clutch device, and in response to detecting the user action to exit the application mode, cause the plurality of surgical tools to be unlocked, and update and display the first graphical user interface at the surgeon console.

One example non-transitory computer-readable medium comprises processor-executable instructions to cause a processor to generate and display a first graphical user interface at a surgeon console associated with a robotic surgical device during a robotic surgical procedure, wherein the robotic surgical device comprises a plurality of surgical tools, the surgeon console comprises a plurality of control devices configured to control the plurality of surgical tools to perform the robotic surgical procedure, the plurality of control devices comprise a clutch device configured to, when activated, cause the plurality of surgical tools locked, and the first graphical user interface is configured to display information related to the robotic surgical procedure and is non-interactive; detect a combination of user actions through the plurality of control devices, wherein the combination of user actions causes the surgeon console to operate in an application mode, and wherein the combination of user actions comprises activating the clutch device; in response to detecting the combination of the user actions, cause the plurality of surgical tools to be locked, and generate and display a second graphical user interface at the surgeon console, wherein the second graphical user interface comprises user interfaces of one or more applications and is configured to be interactive through one or more of the plurality of control devices; detect a user action to exit the application mode, wherein the user action to exit the application mode comprises at least releasing the clutch device; and in response to detecting the user action to exit the application mode, cause the plurality of surgical tools to be unlocked, and update and display the first graphical user interface at the surgeon console.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of certain examples.

FIG. 3C shows another example of the layout of the surgeon console user interface, according to certain aspects of the disclosure;

FIGS. 6A and 6B show an example method for operating the surgeon console user interface in a surgery mode and an application mode, according to certain aspects of the disclosure.

DETAILED DESCRIPTION

Figure 1:
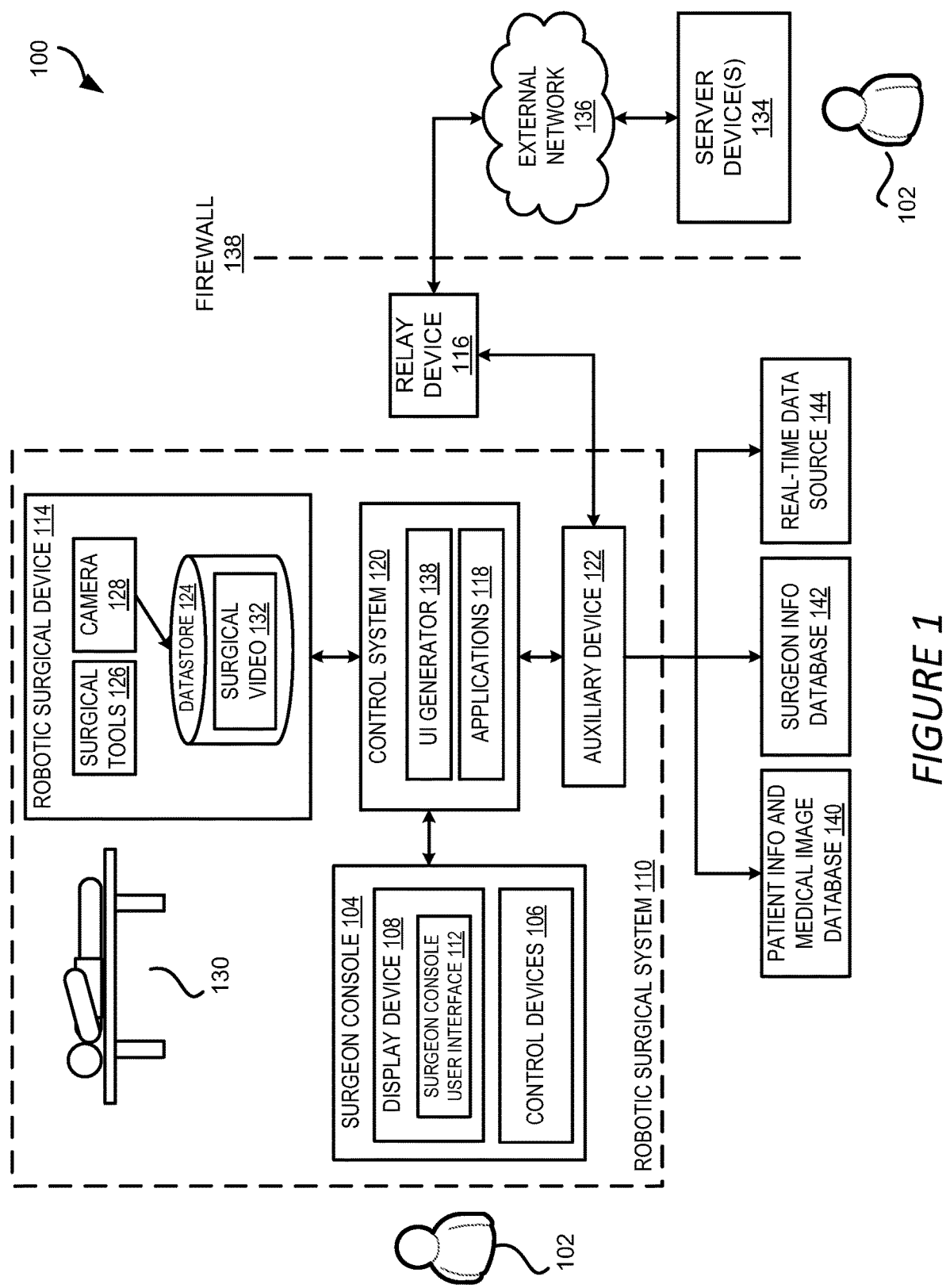
FIG. 1 shows an example of an operating environment for improving the efficiency of robotic surgical procedures by integrating applications into the surgeon console user interface, according to certain aspects of the disclosure.

Examples are described herein in the context of improving the efficiency of robotic surgical procedures by integrating applications into the surgeon console user interface. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example of a robotic surgery system with an improved surgeon console user interface, one or more surgical tools are loaded by a robotic surgical device using respective robotic arms. A surgeon can operate these surgical tools through control devices installed at a surgeon console. To ensure safety during robotic surgery, it is important for a surgeon to be able to visually monitor the operation site. Thus, a camera, such as an endoscope, is also loaded by the robotic surgical device to capture video of a surgical procedure performed using the loaded surgical tools. A surgeon console user interface is presented on the surgeon console to allow the surgeon to view the video of the surgical procedure so that the surgeon can visually monitor the surgical procedure. Other data, such as robotic information, clinical information, can also be displayed in the surgeon console user interface to facilitate the surgeon performing the surgery.

The surgeon console user interface according to the present disclosure includes a main region dedicated to displaying the video signal captured by the camera of the robotic surgical device. The surgeon console user interface further includes a left side region placed at the left side of the main region and a right side region placed at the right side of the main region. The left side region is configured to display data related to the surgical tools controlled by a left hand controller and the right side region is configured to display data related to the surgical tools controlled by a right hand controller.

The surgeon console operates in two modes: a surgery mode and an application mode. In the surgery mode, the surgery is ongoing and the surgical tools and robotic arms are active to enable the surgeon to control the surgical tools using the left-hand and right-hand controllers. The surgeon console user interface is configured to be non-interactive so that the surgeon is not distracted from the surgery. In the application mode, the surgical procedure is paused and the surgical tools and robotic arms are locked. In this mode, the surgeon console user interface integrates and displays applications that are interactive. The surgeon can use control devices to interact with these applications for various purposes, such as to obtain additional information useful for the surgical procedure (e.g. the medical images of the patient), enable certain functionalities to assist the surgical procedure (e.g. turn on a timer).

The surgeon console switches between the application mode and the surgery mode through certain actions performed using the control devices. For example, to switch from the surgery mode to the application mode, activating a clutch device configured for locking or unlocking surgical tools and robotic arms is involved. In one example, the clutch device is a clutch pedal. Switching from the application mode back to the surgery mode involves releasing the clutch device, which also causes the surgical tools and robotic arms to be unlocked. In other words, the actions to be performed by a surgeon to lock (or unlock) the surgical tools and robotic arms and the actions for switching from the surgery mode to the application mode (or switching from the application mode to the surgery mode) share at least a common action so that the surgeon is not confused by which mode he is operating in.

The technology presented herein improves the efficiency of the robotic surgery system. During a robotic surgical procedure, a surgeon may need information from an external system, such as the vital information or medical images of the patient, to facilitate decision-making during the surgical procedure. Accessing this external information during the surgical procedure would require the surgeon to operate another device or log into another system, which causes delays to the surgical procedure and thus reduce the efficiency of the surgical procedure. Integrating useful applications into the surgeon console user interface as described herein eliminates the need for the surgeon to log into another system to retrieve information and access functionalities. As such, the delay of the surgical procedure is reduced and the efficiency is proved. Further, the technology presented here can also improve surgical decision making. Presenting information such as patient vital data, patient medical image in the surgeon console user interface allows the surgeon to view the image side by side with the actual endoscope image (i.e. patient anatomy) rather than relying on memory on the information gathered from a different device. This reduces the chances of making errors in surgical decision.

In addition, the safety of the surgical procedure is not compromised by integrating these applications into the surgeon console user interface. User interfaces of the applications are rendered interactive only in the application mode wherein the surgical tools and robotic arms are locked. As such, the surgeon will not be able to control the surgical tools when interacting with the applications thereby eliminating the chances of operating the surgical tools by mistake. The actions for switching between modes and for locking and unlocking surgical tools and robotic arms are consistent so that the surgeon is not confused with the mode of operation. In addition, the user interfaces or content of the applications or other information on the surgeon console user interface are displayed on the side regions without blocking or otherwise interfering with the video signal of the operating site. As a result, the surgeon is able to monitor the operations of the surgical tools without much distraction from the information or user interfaces presented on the side regions.

This illustrative example is given to introduce the reader to the general subject matter discussed herein and the disclosure is not limited to this example. The following sections describe various additional non-limiting and non-exhaustive examples and examples of improving the efficiency of robotic surgical procedures by integrating applications into the surgeon console user interface.

Referring now to FIG. 1, FIG. 1 shows an example of an operating environment 100 for improving the efficiency of robotic surgical procedures by integrating applications into the surgeon console user interface. The operating environment 100 includes a robotic surgical system 110 configured to assist a surgeon 102 to perform surgical procedures on patients, and various data sources that can be used to obtain useful information for the surgical procedure, such as patient information and medical image database 140, surgeon information database 142, real-time data source 144, and so on. The operating environment 100 also includes a relay device 116 to facilitate the communications of the robotic surgical system 110 with external systems, such as server device(s) 134.

The robotic surgical system 110 includes a robotic surgical device 114 configured to operate on a patient 130. The robotic surgical system 110 also includes a surgeon console 104 that is connected to the robotic surgical device 114 through a control system 120. The surgeon console 104 is configured to be operated by a surgeon 102 in order to control and monitor the surgeries performed via the robotic surgical device 114. The robotic surgical system 110 might include additional stations (not shown in FIG. 1) that can be used by other personnel in the operating room, for example, to view surgery information, video, etc., sent from the robotic surgical device 114. The robotic surgical device 114, the surgeon console 104, the control system 120 and other stations can be connected directly or through a network, such as a local-area network ("LAN"), a wide-area network ("WAN"), the Internet, or any other networking topology known in the art that connects the robotic surgical device 114, the control system 120, the surgeon console 104 and other stations.

The robotic surgical device 114 can be any suitable robotic system that can be used to perform surgical procedures on a patient. A robotic surgical device 114 may have one or more robotic arms connected to a base. The robotic arms may be equipped with one or more surgical tools 126 to perform aspects of a surgical procedure. The surgical tools 126 can include, but are not limited to, tools for grasping for holding or retracting objects, such as forceps, graspers, and retractors, tools for suturing and cutting, such as needle drivers, scalpels and scissors, and other tools that can be used during surgery. Each of the surgical tools 126 can be controlled by the surgeon 102 via operating the control devices 106 on the surgeon console 104. For example, the control devices 106 might include one or more hand controllers, pedals or other types of control devices. Controlling the surgical tools 126 may be performed by the surgeon 102 squeezing, pressing, rolling the hand controllers or pressing one or more pedals. The control devices 106 might also include a clutch device that can be used to lock the surgical tools 126 and the robotic arms. Additional examples of the control devices 106 are provided below with regard to FIG. 2.

In addition, the robotic surgical device 114 may be equipped with one or more cameras 128, such as an endoscope camera, configured to provide a view of the operating site to guide the surgeon 102 during the surgery. In some examples, the camera 128 can be attached to one of the robotic arms of the robotic surgical device 114. In other examples, the camera 128 can be attached to a mechanical structure of the robotic surgical device 114 that is separate from the robotic arms.

Different robotic surgical devices 114 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one robotic surgical device 114 is depicted, any suitable number of robotic surgical devices may be employed within a robotic surgical system 100.

In some examples, the robotic surgical device 114 may be configured to record data during a surgical procedure. For example, images and videos of the surgical procedures performed by the robotic surgical device 114 can also be recorded and stored for further use. For instance, a datastore 124 can be employed by the robotic surgical device 114 to store surgical videos 132 of surgical procedures captured by the camera 128. It should be understood that while FIG. 1 shows that the surgical videos 132 are stored in the datastore 124 of the robotic surgical device 114, the surgical videos 132 may be stored on other devices of the robotic surgical device 110, such as the control system 120.

In the example shown in FIG. 1, surgical video 132 of a robotic surgical procedure captured by the camera 128 can also be transmitted to the surgeon console 104 and be displayed in a surgeon console user interface 112 on a display device 108. In some configurations, the surgical video 132 is displayed in real-time so that the surgeon 102 can view the procedure while the surgical tools 126 are being operated on the patient 130. In some examples, the control system 120 is configured to generate the surgeon console user interface 112 for display at the surgeon console 104.

In the example shown in FIG. 1, the control system 120 includes a UI generator 138 for generating the surgeon console user interface 112. The UI generator 138 generates the surgeon console user interface 112 according to the mode of the surgeon console 104. In some examples, the surgeon console 104 can operate in two modes: a surgery mode and an application mode. In the surgery mode, the surgical tools 126 of the robotic surgical device 114 can be controlled by the surgeon 102 via the control devices 106 at the surgeon console 104. Thus the surgical procedure proceeds as normal in the surgery mode. In the application mode, the surgical tools 126 and their associated arms are locked and the control devices 106 cannot be utilized to control the surgical tools 126 to perform the surgical operations.

Switching between the surgery mode and the application mode is performed through a certain action or a certain combination of actions by the surgeon 102. In one example, the surgeon console 104 is switched from the surgery mode to the application mode when the surgeon 102 performs a combination of activating a clutch device to lock surgical tools 126 and robotic arms and activating one or more handle controllers. The surgeon console 104 remains in the application mode until the clutch device is released, by which time, the surgeon console 104 returns to the surgery mode. Other actions can be utilized to switch between the two modes.

When the surgeon console 104 operates in the surgery mode, the UI generator 138 generates the surgeon console user interface 112 with information that is needed during the surgical procedure and renders the surgeon console user interface 112 non-interactive. In one example, the surgeon console user interface 112 in the surgery mode presents the surgical video 132, the status information of the surgical tools 126, and the status of the camera. The surgeon console user interface 112 in this mode cannot be interacted with by the surgeon 102 so that the surgeon 102 is not distracted by the surgeon console user interface 112. Further, because the surgeon console user interface 112 is not interactive and the surgeon 102 cannot operate on the surgeon console user interface 112, the surgeon 102 will not be confused by whether his actions are applied to the robotic surgical device 114 or the surgeon console user interface 112.

When the surgeon console 104 operates in the application mode, the UI generator 138 adds user interfaces of various applications 118 to the surgeon console user interface 112 to provide additional information and functionalities. For example, the applications 118 can include an application for obtaining and displaying patient vital data, a medical image application that allows the surgeon 102 to browse through patient medical images, or a stadium view application that presents a three-dimensional (3D) model of the robotic surgical device 114. The applications 118 can further include other applications, such as a timer to measure time intervals, an ICG application for adding an indocyanine green (ICG) layer to the surgical video 132, an annotation application for adding annotations to the surgical video 132, and other applications.

To obtain the information used in the applications 118, the robotic surgical system 110 employs an auxiliary device 122 that is in communication with various data sources. The data sources can include, for example, the patient information and medical image database 140 for obtaining patient information and medical images (e.g. name, age, gender, BMI, CT scan images, MRI images, etc.), the surgeon information database 142 for retrieving basic surgeon information (e.g. name, age, gender, expertise, etc.), and the real-time data source 144 for obtaining real-time data such as real-time data from an ultrasound probe applied to the patient 130, patient vital data, patient electrocardiogram data, and so on.

Depending on where these databases are located, the auxiliary device 122 may need to communicate with the database through one or more networks. If the database is located within the hospital network where the robotic surgical system 110 is located, then the auxiliary device 122 communicates with the database through an internal network. If the database is located outside the hospital network, the auxiliary device 122 may need to communicate with the database through an external network. In the latter case, instead of the auxiliary device 122 communicating with the database through the external network, the auxiliary device 122 can, in one example, communicate with a relay device 116 located on the internal network, and the relay device 116 communicates with the database through the external network. The relay device 116 can be a gateway, a hub, a server computer, or any other computing device capable of connecting to the hospital network to communicate with the auxiliary device 122 and connecting to the external network 136 via a firewall 138 to communicate with devices outside the hospital network, such as the external database, or the server devices 134.

After the auxiliary device 122 receives the data from the various data sources, the auxiliary device 122 can filter the data based on the requirement of the applications 118. In another example, the auxiliary device 122 forwards the collected data to the applications 118 and the applications 118 filter or select the data based on what is to be used and presented in the respective applications 118.

In addition, the auxiliary device 122 is further configured to store the surgical video 132 along with annotations added to the surgical video 132 through the annotation application, and upload the surgical video 132 to one or more server device(s) 134. In some examples, the surgical video 132 is uploaded to the relay device 116 which further transmits the surgical video 132 to the server devices 134 through the external network 136.

In some implementations, not all the applications 118 are presented in the surgeon console user interface 112 when the surgeon console 104 is in the application mode. In these implementations, the surgeon 102 can specify, before the surgical procedure starts, his or her preferences regarding the applications 118 to be presented in the surgeon console user interface 112 through, for example, an online service hosted by the server device 134. The surgeon 102 may utilize the online service to view the applications 118 that are available in the surgeon console user interface 112 when the surgeon console 104 operates in the application mode. The surgeon 102 may further utilize the online service to specify or select the applications that the surgeon 102 prefers to view during a particular surgical procedure. In other words, the preference can be specified for a particular surgeon and for a particular surgical procedure.

In addition to the applications to be included in the surgeon console user interface 112, the surgeon 102 may also utilize the online service hosted by the server devices 134 to specify other parameters associated with the surgeon console user interface 112, such as the size of the surgeon console user interface 112 including the width, height, aspect ratio, etc., the background color, the font, and so on. The server devices 134 saves and transmits the surgeon preferences to the relay device 116, which forwards the preferences to the auxiliary device 122 and then to the control system 120. Based on the preferences, the UI generator 138 can generate the surgeon console user interface 112 with the specified parameters and include the applications that are preferred by the surgeon 102 and exclude the applications that are not preferred by the surgeon 102.

While using the surgeon console user interface 112, the surgeon 102 may further adjust the parameters of the surgeon console user interface 112. These adjustments can be detected by the control system 120 and transmitted to the server devices 134 to update the surgeon preferences. The updated preferences will be loaded on a robotic surgical system 110 that the surgeon 102 will use for future surgical procedures.

It should be understood that while FIG. 1 shows that the auxiliary device 122 is a separate device from the control system 120, they can be implemented on one device in some examples. For instance, the functionalities of the auxiliary device 122 may be implemented in the control system 120 to eliminate the need for a separate auxiliary device 122. In other examples, the auxiliary device 122 may be a device external to the robotic surgical system 110 and in communication with the robotic surgical system 110 through the hospital network. In addition, the server device 134 may represent one or more conventional server computers, Web servers, cloud servers, database servers, or network appliances. Alternatively, the server device 134 may represent a user computing device, such as a PC, a desktop workstation, a laptop, a notebook, a mobile device, and the like. It will be appreciated that the server device 134 may represent any server computers or user computing devices known in the art.

As discussed above, in the application mode, some of the user interfaces of the applications 118 are interactive. In this mode, the surgeon console user interface 112 becomes interactive and can receive input from the surgeon 102. In one example, the surgeon 102 interacts with the surgeon console user interface 112 via one or more of the control devices 106. Since in the application mode, the surgical tools 126 and robotic arms are locked, operating the control devices 106 would not cause the surgical tools 126 and the robotic arms to move. As such, the surgeon 102 can use the control devices 106 to interact with the applications 118 presented in the surgeon console user interface 112. Additional details regarding the applications 118 and how to interact with these applications 118 are provided below with respect to FIGS. 5A-6B. Additional details regarding the control devices 106, the surgeon console 104 and the surgeon console user interface 112 in the surgical mode are provided below with regard to FIGS. 2-4D.

Figure 2:
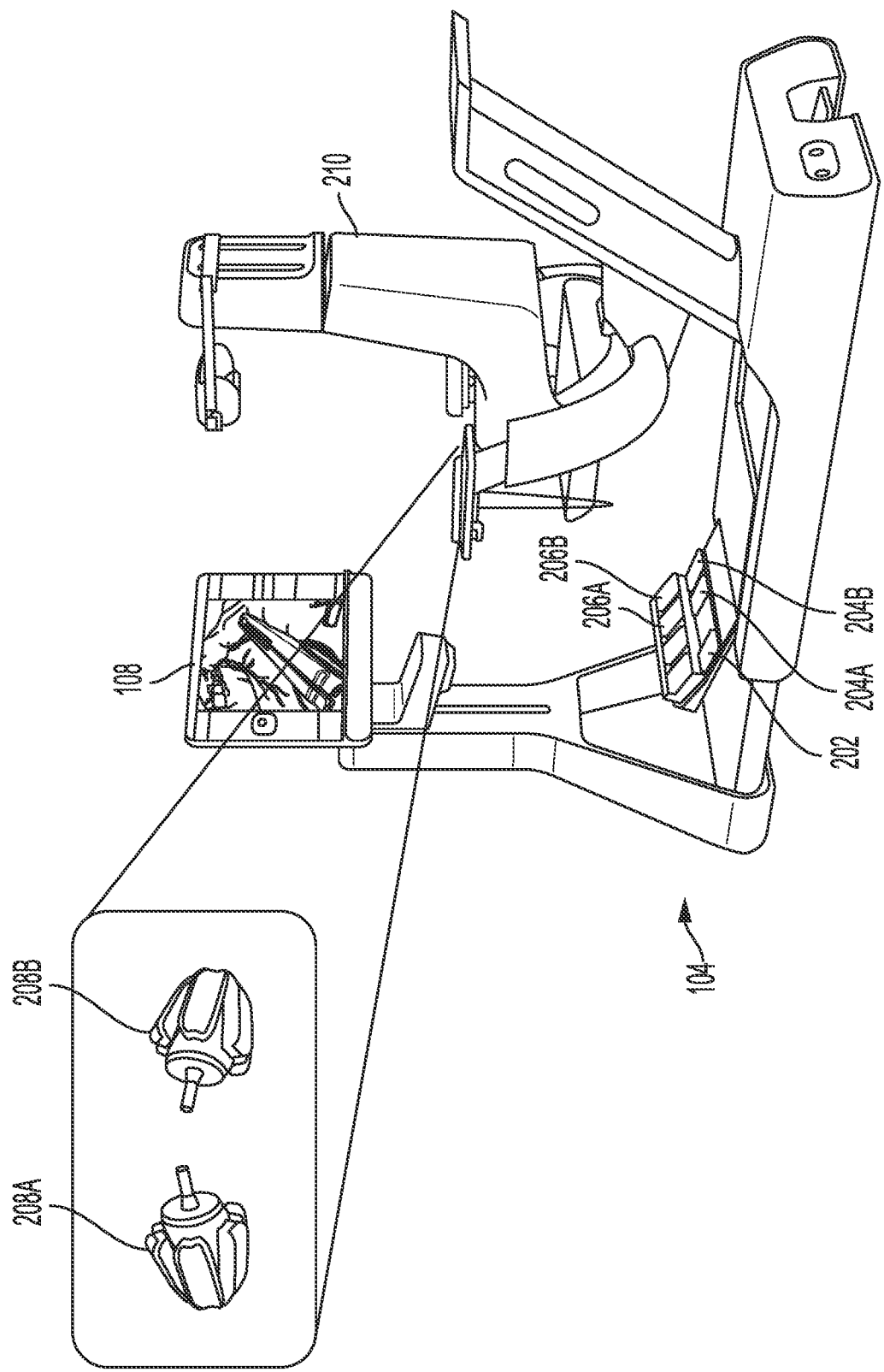
FIG. 2 shows a diagram of an example surgeon console, according to certain aspects of the disclosure.

Referring now to FIG. 2, where a diagram of an example of the surgeon console 104 is presented according to certain aspects of the disclosure. The surgeon console 104 shown in FIG. 2 includes a display device 108, a surgeon seat 210, and a set of control devices 106. In this example, the control devices 106 includes two hand controllers 208A and 208B, a clutch pedal 202 and pedals 204A, 204B, 206A, 206B for controlling the surgical tools 126. Other control devices may be included, such as a pedal for moving the camera 128, or a pedal for changing the tool and robotic arm operated by a hand controller to another tool and robotic arm.

The clutch pedal 202 is configured for locking and unlocking the surgical tools 126 and the robotic arms of the robotic surgical device 114. In some configurations, the surgical tools 126 and robotic arms are locked when the clutch pedal 202 is pressed and are unlocked when the clutch pedal 202 is released.

When the surgeon console 104 is in the surgery mode, the hand controllers 208A and 208B (which may be referred to herein individually as a hand controller 208 or collectively as the hand controllers 208) are configured to control the surgical tools 126 based on the operations of the surgeon 102. The surgeon 102 may press, tab, squeeze, roll or otherwise operate on the hand controllers 208 to control the surgical tools 126 to move, cut, suture, roll depending on the type of the surgical tools. In some configurations, one hand controller 208A (referred to as the left hand controller) is operated by the left hand and the other hand controller 208B (referred to as the right hand controller) is operated by the right hand.

The pedals 204A, 204B, 206A, and 206B are organized in two pairs: one pair of pedals 204A and 206A, and the other pair of pedals 204B and 206B. In some configurations, the pair of pedals 204A and 206A are operated by the left foot; and the pair of pedals 204B and 206B are operated by the right foot. Each of these two pairs of pedals is configured to control a surgical tool in the surgery mode and apply force or energy to the operations performed by the surgical tool. The pedals 204A and 206B are associated with the hand controller 208A so that the action performed by the pedal 204A or 206B is applied to the surgical tool 126 controlled by the hand controller 208A. For example, if the hand controller 208A is used to control a pair of scissors, the pedals 204A and 206A can be configured to apply a certain level of energy on the scissors to perform the actions "cut" and "coagulate," respectively. It should be noted that for some surgical tools, there is no more than one action associated therewith. As a result, only one pedal or no pedal is associated with those tools.

As discussed above with regard to FIG. 1, the clutch pedal 202 can be utilized to switch between the surgery mode and the application mode. In some examples, the application mode is invoked by a combination of actions involving the clutch pedal 202. For example, the surgeon console 104 can be configured to enter the application mode if the surgeon 102 presses the clutch pedal 202 and in the meanwhile activates one or both hand controllers 208. Activating the hand controllers 208 may be performed by squeezing, pressing, tabbing one or both hand controllers 208 for more than a threshold value of time duration, such as 3 seconds. Once the surgeon console 104 enters the application mode, the surgeon 102 can release the hand controllers 208. However, in order to remain in the application mode, the clutch pedal 202 need to be pressed so that the surgical tools 126 and robotic arms remain locked.

In the application mode, the hand controllers 208 can be reconfigured to interact with the surgeon console user interface 112 under the control of the surgeon 102. For example, one or both hand controllers 208 can be used to select the user interface controls, browse through content presented in the surgeon console user interface 112, set parameter values for an application 128, and so on. Detailed examples of interacting with the surgeon console user interface 112 are provided below with regard to FIGS. 5A-5E. Other control devices 106 or other user interface devices may also be utilized to interact with the surgeon console user interface 112 in the application mode. For example, if the display device 108 is configured with a touch screen, the surgeon 102 can utilize the touch screen to interact with the surgeon console user interface 112. In addition, if the surgeon console 104 is configured with other types of user interface devices, such as a touchpad, the touchpad can be configured to allow the surgeon 102 to interact with the surgeon console user interface 112.

The surgeon console 104 returns to the surgery mode when the clutch pedal 202 is released. When in the surgery mode, the surgeon 102 controls the surgical tools 126 through the control devices 106 as discussed above.

To support the switch between the surgery mode and the application mode, in one example, the control system 120 is configured to detect the status of the clutch pedal 202. If the clutch pedal 202 is released, the control system 120 determines that the surgeon console 104 is in the surgery mode and the control system 120 passes the control signal generated by the control devices 106 to the robotic surgical device 114 to control the surgical tools 126. If the control system 120 detects that the clutch pedal 202 is pressed, the control system 120 further detects if the combination of actions to enter the application mode has been performed.

In the example where the combination of actions includes the activation of the clutch pedal 202 and one or both hand controllers 208, the control system 120 detects whether the one or both hand controllers 208 are activated for the required time duration. If the combination of actions is not detected, the control system 120 determines that the surgeon console 104 is still in the surgery mode and passes the control signals from the control devices 106 to the robotic surgical device 114.

If the control system 120 detects the combination of actions, the control system 120 determines that the surgeon console 104 is in the application mode and instructs the UI generator 138 to generate the surgeon console user interface 112 to include the applications 118. The control system 120 further passes the control signals received from the control devices 106 to the respective applications 118, instead of forwarding them to the robotic surgical device 114. In this way, the surgeon 102 can interact with the applications 118 using the same set of control devices 106 that are used to control the surgical tools 126. Using the same set of control devices 106 for the surgery mode and the application mode allows the surgeon 102 to smoothly switch between these two modes without switching between different controlling devices, thereby increasing the efficiency of the surgical procedure.

The control system 120 continues to detect the status of the clutch pedal 202. Once the control system 120 detects that the clutch pedal 202 has been released, the control system 120 instructs the UI generator 138 to generate the surgeon console user interface 112 for the surgery mode and forwards subsequent control signals received from the control devices 106 to the robotic surgical device 114.

It should be understood that while the above description focuses on using the clutch pedal 202 to initiate the switching between the two modes of the surgeon console, other control devices 106 can also be utilized to implement the mode switch, such as hand controller buttons, hand controller gesture, or other pedals. When other control devices are used to switch the surgeon console between the application mode and the surgery mode, similar operations can be performed by the control system 120 to detect the mode of the surgeon console and present the surgeon console user interface accordingly.

Figure 3:
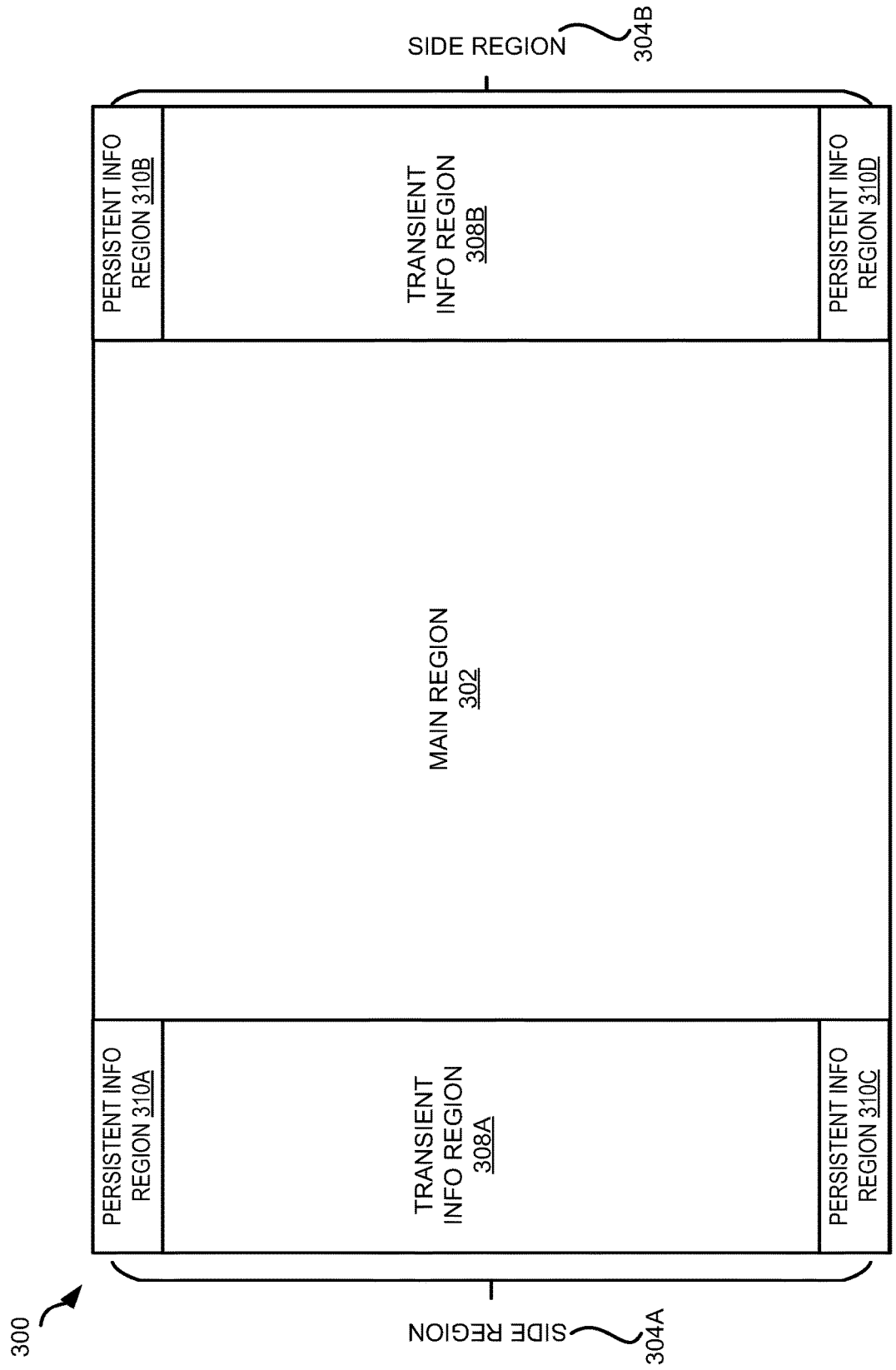
FIG. 3 shows an example of a layout of the surgeon console user interface, according to certain aspects of the disclosure.

FIG. 3 shows an example of a layout 300 of the surgeon console user interface 112, according to certain aspects of the disclosure. In this example, the layout 300 of the surgeon console user interface 112 includes three areas: a main region 302, a left side-region 304A and a right side-region 304B (which may also be referred to herein individually as a side region 304 or collectively as the side regions 304). When the surgeon console 104 operates in the surgery mode, the main region 302 is dedicated to displaying the surgical video 132 of the operating site captured by the camera 128 of the robotic surgical device 114. In some examples, the main region 302 is used to display only the surgical video 132. In other examples, the main region 302 is also used to display non-critical information related to the surgical procedure at one or more corners of the main region 302 or to display critical information in the middle of the main region 302.

The left and right side regions 304 are utilized to display complementary information related to the surgical procedure. The left side region 304A is placed at the left side of the main region 302 and the right side region 304B is placed at the right side of the main region 302. In some examples, the information displayed in the side regions 304 can be categorized into three types: persistent information, application user interfaces, and transient messages. Persistent information pertains to the configuration of the robotic surgical device 114 and is needed throughout the surgical procedure. The persistent information includes details such as the status of the robotic arms (e.g. active or inactive), tools connected to each of the arms, actions associated with the respective pedals 204 or 206, information about the camera 128, and so on. In some examples, the status of the surgical tools 126 controlled by the left hand controller 208A is shown in the left side region 304A and the status of the surgical tools 126 controlled by the right hand controller 208B is shown in the right side region 304B.

Transient messages include non-critical messages to be displayed to the surgeon 102 during the surgical procedure, such as a message informing the surgeon 102 that a surgical tool is approaching the workspace limit. This type of message will disappear after a pre-determined amount of time, such as 5 seconds. Displaying the non-critical message in the side regions 304 in a transient manner can keep the camera view (i.e. the surgical video 132) as clean and distraction-free as possible.

Application user interfaces are displayed in the right and left side regions 304 when the surgeon console 104 is switched to the application mode. The application user interfaces are removed from the side regions 304 when the surgeon console 104 exits the application mode. As such, the application user interfaces are also displayed transiently to minimize the distractions to the surgeon 102.

In the example shown in FIG. 3, each of the side regions 304 is divided into two types of regions: persistent information regions 310A-310D and transient information regions 308A and 308B. The persistent information regions 310A-310D are located at the very top and bottom of the side regions 304. The transient information regions 308A and 308B fill in the remaining space of the respective side region. With this layout, in the surgery mode, the side regions only display the persistent information in the persistent information region 310A-310D, leaving the middle portion (i.e. the transient information regions 308A and 308B) blank to prevent distraction and unnecessary visual noise. When the surgeon console 104 enters the application mode, the user interfaces of the applications fill the rest of the space on those side regions (i.e. the transient information regions 308A and 308B). In some examples, the side regions 304A or 304B also have distinct visual treatment when the surgeon console enters the application mode, such as changing color, showing lock icons, etc. These visual treatments help to remind the surgeon that the surgeon console is in the application mode and that the robotic arms and surgical tools are locked.

It should be understood that while FIG. 3 shows a particular example of the layout of the surgeon console user interface 112, other layouts can also be used for the surgeon console user interface 112. For example, instead of each of the side regions 304 including two persistent information regions 310, any number of persistent information regions 310 can be included in a side region 304. For example, the left side region 304 includes one persistent information region 310 on the top or the bottom, while the right side region 304 includes two persistent information regions 310; or vice versa. In another example, both side regions 304 include one persistent information region 310 on the top or bottom of the respective side region 304. Other arrangements of the persistent information regions 310 within the side regions 304 are also possible. Likewise, the side regions 304 can be arranged differently than that shown in FIG. 3. For example, both side regions 304 can be placed on one side of the main region 302, such as the left side, right side, top side or bottom side of the main region 302. In addition, more than two side regions 304 can be employed. These side regions 304 can be placed around the main region 302 in any matter. FIGS. 3A-3E show examples of alternative layouts for the surgeon console user interface 112.

Figure 3A:
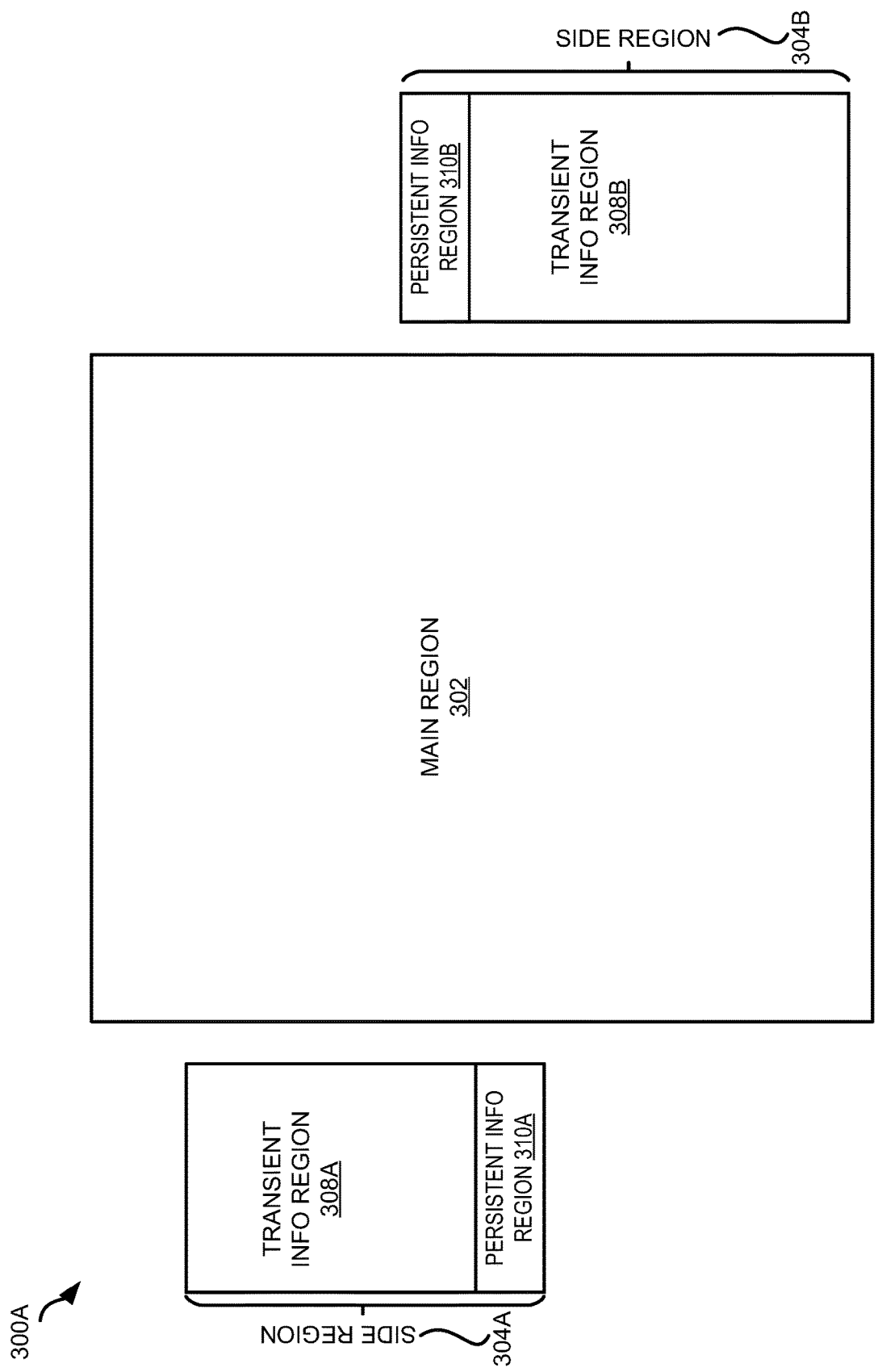
FIG. 3A shows another example of the layout of the surgeon console user interface, according to certain aspects of the disclosure.

FIG. 3A shows an example of a layout 300A of the surgeon console user interface 112, according to certain aspects of the disclosure. In this example, the side region 304A is placed on the left side of the main region 302, but not necessarily adjacent to the main region 302. Similarly, the side region 304B is placed on the right side of the main region 302, but not necessarily adjacent to the main region 302. In addition, the side regions 304A and 304B may have different shapes or sizes or have the same height as the main region 302. The number of persistent information regions 310 in the side regions 304 may be the same or different. The locations of the persistent information regions 310 within their respective side regions 304 may be different. For example, the persistent information region 310A is placed at the bottom of the side region 304 and the persistent information region 310B is placed at the top of the side regions 304B. In other examples, the persistent information region(s) 310 can be placed anywhere in the respective side regions 304. Similarly, there may be more than one transient information region 308 in a side region 304 and the locations of the transient information regions 308 can be anywhere within the respective side regions 304.

Figure 3B:
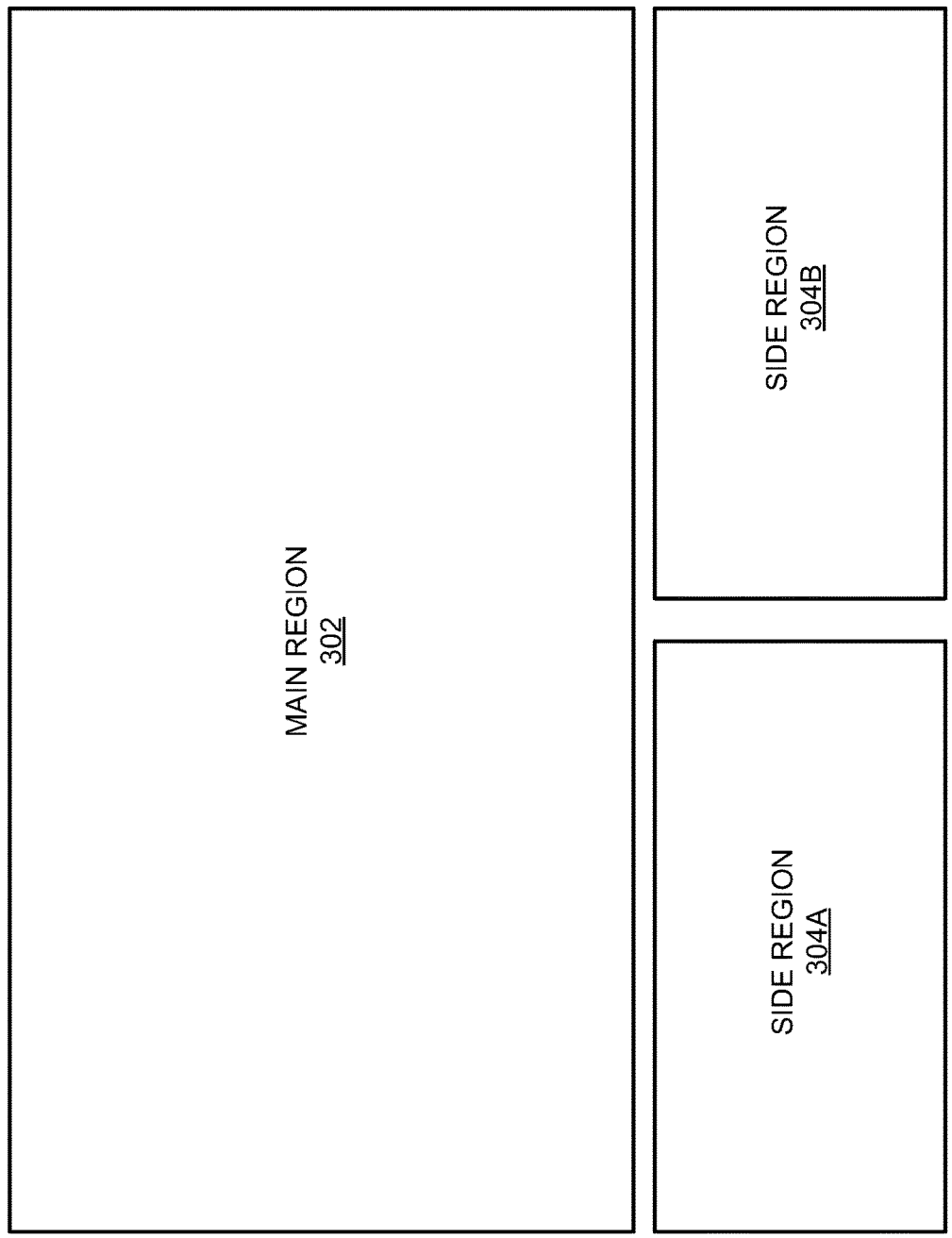
FIG. 3B shows another example of the layout of the surgeon console user interface, according to certain aspects of the disclosure.

FIG. 3B shows another example of a layout 300B of the surgeon console user interface 112, according to certain aspects of the disclosure. In this example, the left side region 304A and the right side region 304B are shown below the main region 302. Similarly, the left side region 304A and the right side region 304B can also be shown above the main region 302. FIG. 3C shows yet another example of a layout 300C of the surgeon console user interface 112. In this example, the left side region 304A is placed above the main region 302 and the right side region 304B is placed below the main region 302. In another example, the left side region 304A and the right side region 304B are reversed and placed below and above the main region 302, respectively. In the examples of Figures B and C, each of the side regions 304 can have a different size and shape than the other. Each of the side regions 304 can be adjacent to the main region 302 or have a certain distance from the main region 302.

Figure 3D:
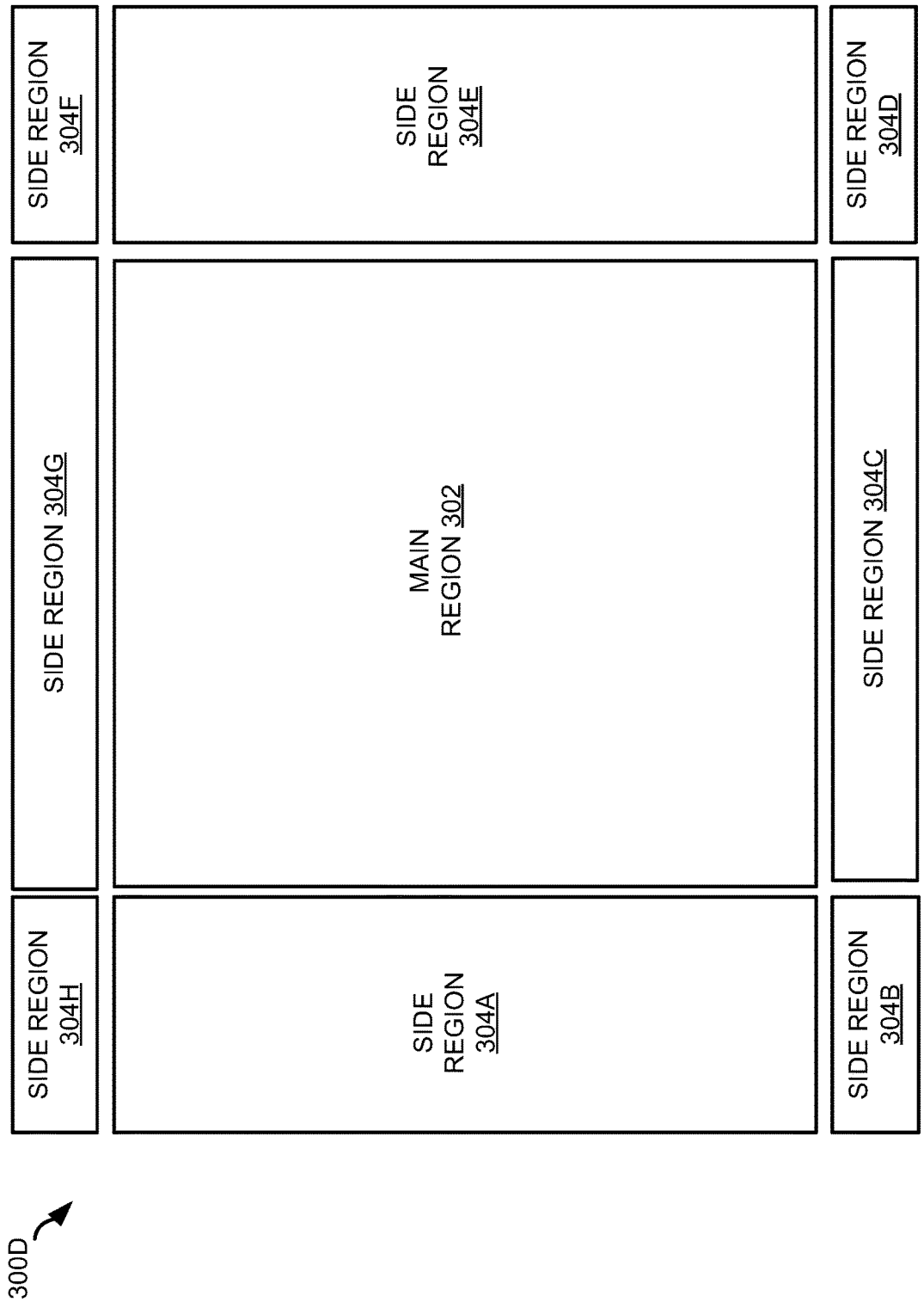
FIG. 3D shows another example of the layout of the surgeon console user interface, according to certain aspects of the disclosure.

FIG. 3D shows another example of a layout 300D of the surgeon console user interface 112, according to certain aspects of the disclosure. In this example, there are more than two side regions 304 in the surgeon console user interface 112 and these side regions 304 are placed around the main region 302. Each of the side region 304 can have any number of transient information regions 308 or persistent information regions 310, such as 0, 1, 2, and so on. In addition, although the side regions 304 are shown as rectangles in FIG. 3B, they can be presented in any shape (e.g. circle, triangle, oval, L-shaped, U-shaped, etc.) and the shapes for different side regions 304 may be the same or different. Further, each region shown in FIG. 3B may be adjacent to its neighboring regions or have a certain distance from its neighboring regions. It should be understood that although FIG. 3B shows eight side regions 304, there can be any number of side regions 304 in the surgeon console user interface 112.

Figure 4A:
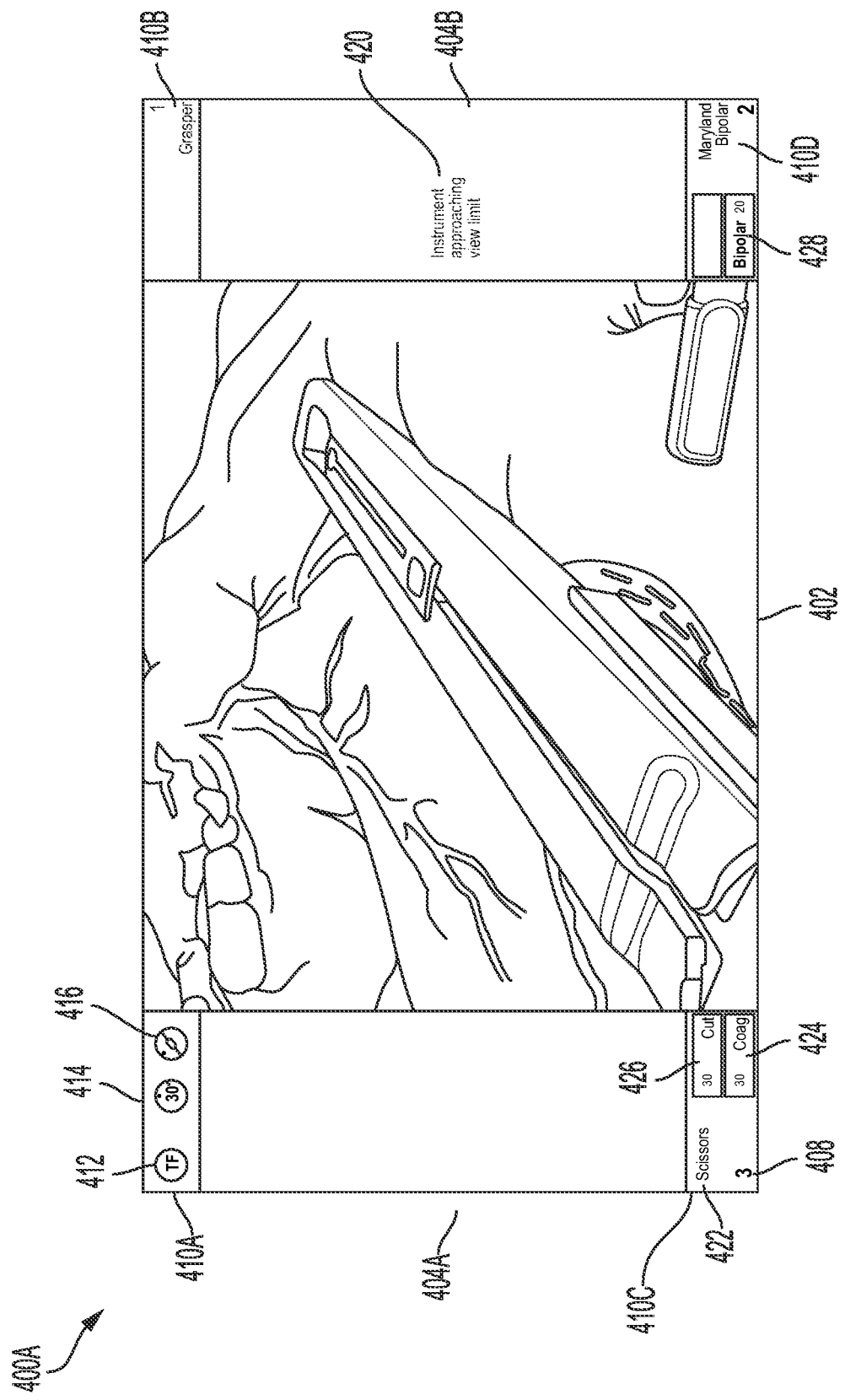
FIG. 4A shows an example of the surgeon console user interface in a surgery mode, according to certain aspects of the disclosure.

Referring now to FIGS. 4A-4D, where examples of the surgeon console user interface 112 when the surgeon console 104 operates in the surgery mode are shown. The surgeon console user interface 112 shown in these figures and Figures are based on the layout shown in FIG. 3. Surgeon console user interfaces 112 based on other layouts can be generated similarly. FIG. 4A shows an example user interface (UI) 400A of the surgeon console user interface 112 in a surgery mode, according to certain aspects of the disclosure. In the UI 400A, the main region 402 shows the surgical video 132 of the current surgical procedure. The left side region 404A and the right side region 404B show the information complementary to the surgical video 132 including the status of the surgical tools 126, the status of the camera 128 and the surgeon information. In particular, the status of the surgical tools 126 is shown in the persistent information regions 410B-410D and the status of the camera 128 and the surgeon information are shown in the persistent information region 410A.

For example, the persistent information region 410C shows the status of the surgical tool 126 controlled by the left hand controller 208A. In the example shown in FIG. 4A, the surgical tool controlled by the left hand controller is a pair of scissors. The persistent information region 410C shows the name 422 of the tool and the identifier 408 of the robotic arm where the surgical tool is installed. In this example, the pair of scissors is installed on robotic arm 3. The persistent information region 410C further includes a status box 426 showing the action and the energy level of the action performed by the surgical tool when the pedal 206A is activated. In this example, if the pedal 206A is pressed or otherwise activated, a cut action will be performed by the scissors with an energy level of 30. Similarly, a status box 424 is also included to show the action and the energy level of the action performed by the surgical tool when the pedal 204A is activated.

The persistent information region 410D shows the status of the surgical tool 126 controlled by the right hand controller 208B. In the example shown in FIG. 4A, the surgical tool controlled by the right hand controller is a Maryland bipolar. The persistent information region 410D shows the name of the tool and the identifier of the robotic arm where the surgical tool is installed. In this example, the Maryland bipolar is installed on robotic arm 2. The persistent information region 410D further includes a status box 428 showing the action and the energy level of the action performed by the surgical tool when the pedal 204B is activated. The information for the pedal 206B is not shown because the pedal 206B does not apply to this tool.

In some implementations, the pedals 204A, 204B, 206A, and 206B are painted with certain colors. In those cases, the user interface controls in the persistent information regions 410C and 410D associated with the respective pedals, such as the status boxes 424 and 426, are also displayed with a color matching the color of the respective pedals. For example, if the pedals 204A and 204B are painted with a blue color, then the status box 424 for the pedal 204A and the status box 428 for the pedal 204B are also shown in the blue color. If the pedal 206A is painted in yellow color, the status box 426 is also displayed in the yellow color. This can help the surgeon 102 to associate the pedals with the right status boxes, thereby reducing operational errors.

In some examples, the robotic surgical device 114 has four robotic arms, three for loading surgical tools and one for loading the camera 128. If three surgical tools are loaded to the robotic arms, the third tool will stay inactive because each of the two hand controllers can only control one surgical tool. One of the hand controllers, either the left hand controller 208A or the right hand controller 208B, will be configured to control two surgical tools. The surgeon 102 can use this hand controller to switch between these two surgical tools by, for example, pressing a tool switch pedal or through other mechanisms.

In the example shown in FIG. 4A, the right hand controller 208B is used to control two surgical tools. As such, the persistent information region 410B in the right side region 404B is utilized to show the status of the inactive surgical tool controlled by the right hand controller 208B. The status information includes the name of the tool (e.g. grasper) and the robotic arm (arm 1) where the tool is loaded. The persistent information region 410B shows the status of this robotic tool using a different background color or font color than that of the tools shown in the persistent information regions 410C and 410D to indicate that this tool is inactive and is not currently controlled by the corresponding hand controller. In some implementations, the persistent information region 410B also shows the status of the tool jaws (such as closed or open). If the surgeon 102 switches the right hand controller 208B to control the grasper instead of the Maryland bipolar, the persistent information region 410B will show the status of the inactive Maryland bipolar and the persistent information region 410D will show the status of the grasper. The status of the pedals in the persistent information region 410D will also be updated depending on whether the grasper uses both pedals and the type of actions associated with each pedal.

Because the left hand controller 208A is used to control only one surgical tool, the persistent information region 410A in the left side region can be used to show information other than the status of the surgical tool. In the example shown in FIG. 4A, the persistent information region 410A is used to show the surgeon information 412, the status of the camera 128, such as the angle information 414 of the camera and the status of the horizontal line 416 of the camera. Other information can also be shown in the persistent information region 410A.

If the left hand controller 208A is used to control two surgical tools and the right hand controller 208B is used to control one surgical tool, the persistent information region 410A can be configured to show the status information of the inactive tool controllable by the left hand controller 208A. Such spatial arrangement helps the surgeon immediately deduce where the surgical tool is connected. In this situation, the persistent information region 410B can be configured to show information other than the status of the surgical tool, such as the surgeon information and the camera information. In other examples, the non-tool information, such as the surgeon information and the camera information, can be shown in the main region 402 without interfering with the surgical video 132. For example, the camera information may be shown in the upper left corner or the upper right corner of the main region 402 since the focus of the surgical video 132 is the middle and bottom portion where the tools are shown.

In the example shown in FIG. 4A, a non-critical transient message 420 is shown in the transient information region of the right side region 404B to warn the surgeon 102 that the surgical tools are approaching the limit of the camera view. The message will be removed after a pre-determined amount of time or when the condition causing the generation of the warning message no longer exists, such as when the tools are back in the center of the camera view.

Figure 4B:
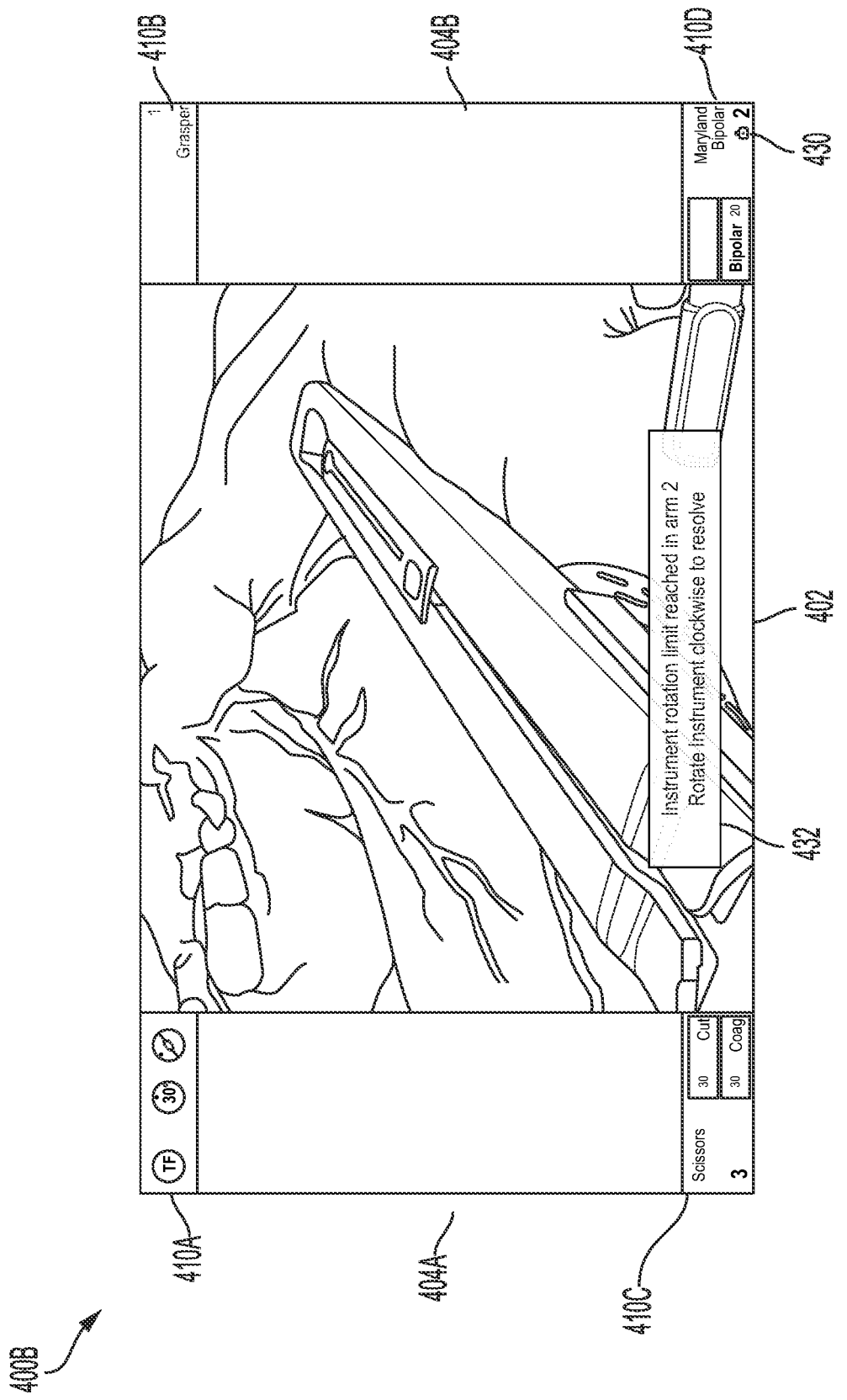
FIG. 4B shows another example of the surgeon console user interface in the surgery mode, according to certain aspects of the disclosure.

FIG. 4B shows another example UI 400B of the surgeon console user interface 112 in the surgery mode, according to certain aspects of the disclosure. UI 400B is similar to UI 400A except that the robotic surgical device 114 now has a critical system issue. In the UI 400B, a message indicating the critical system issue is displayed in a message window 432 overlaying on the center portion of the main region 402 to ensure the surgeon's attention and action. In some implementations, the message window 402 is rendered semi-transparent to avoid complete obstruction of the main region 402. The persistent information region 410D further shows an icon 430 indicating the status of the robotic arm involved in the critical system issue as being locked. The message window 432 will be displayed in the main region 402 until the critical system issue is resolved. By then, if the robotic arm is unlocked, the lock icon 430 will disappear suggesting that the robotic arm has been unlocked.

In some examples, the surgeon console user interface 112 can also be configured to indicate the interaction of the surgeon 102 with the foot pedals. The indication is generated and rendered to balance attention and distractions. In some examples, when the surgeon 102 hovers over an energy pedal, the pedal status box is mildly enhanced to alert the surgeon 102 on his/her foot location in order to prevent unintentional press. If the pedal is pressed, the pedal status box is further enhanced and accompanied by an auditory cue, to provide the surgeon 102 a clear feedback about his/her actions.

Figure 4C:
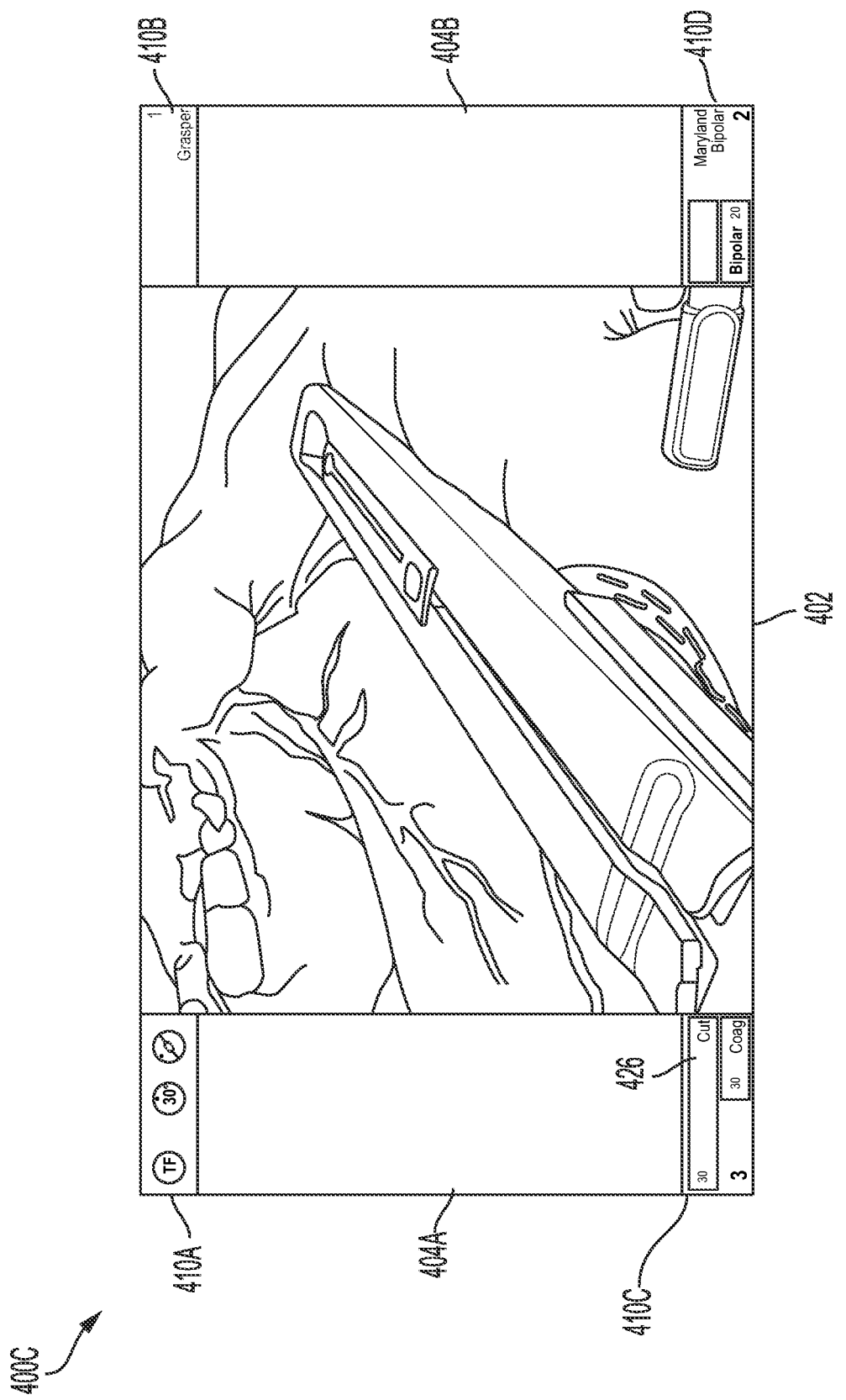
FIG. 4C shows another example of the surgeon console user interface in the surgery mode, according to certain aspects of the disclosure.
Figure 4D:
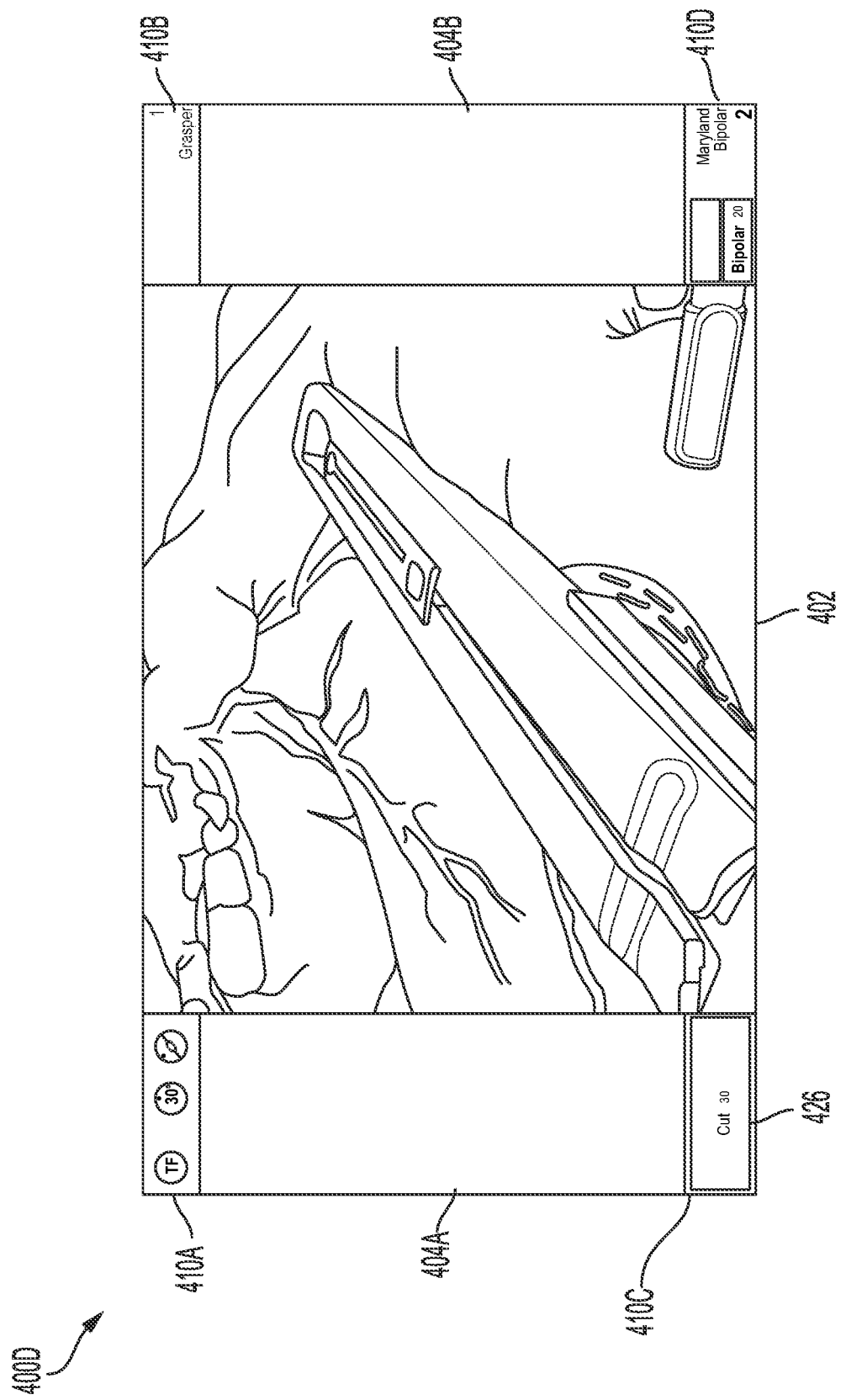
FIG. 4D shows another example of the surgeon console user interface in the surgery mode, according to certain aspects of the disclosure.

FIG. 4C shows an example UI 400C of the surgeon console user interface 112 when the surgeon 102 hovers his/her foot over the pedal 206A. In this example, the pedal status box 426 is enlarged to alert the surgeon 102 that his/her foot is over the pedal 206A. FIG. 4D shows an example UI 400D of the surgeon console user interface 112 when the surgeon 102 presses the pedal 206A. In this example, when the surgeon 102 presses the pedal 206A, the status box 426 is expanded over the entire persistent information region 410C. Other ways of enhancing the status box of the pedal may be utilized. For example, the status box can be expanded over the entire left side region 404A. An amination or a sound can also be produced along with the expansion to provide the feedback to the surgeon 102.

As discussed above, when the surgeon 102 switches the surgeon console 104 to the application mode, such as by pressing the clutch pedal 202 along with activating the hand controllers 208A and 208B, the surgeon console user interface 112 is updated to include one or more applications 118. These applications are presented in the transient information regions 308 of the left and right side regions. Each of the transient information regions 308 may be configured to present no more than a maximum number of simultaneous applications, e.g. two applications, to reduce screen clutter and ensure enough screen space is provided to each application.

Figure 5A:
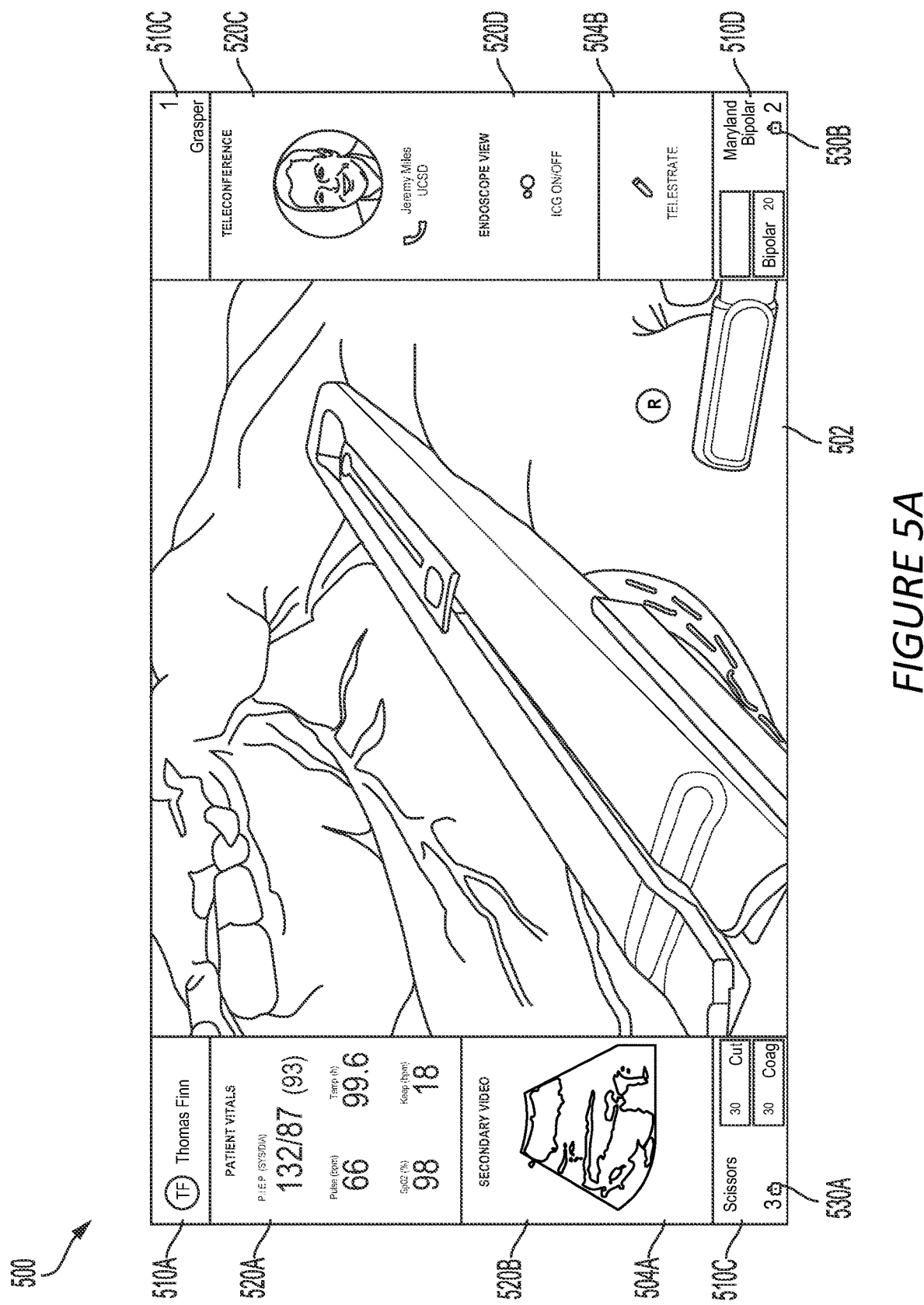
FIG. 5A shows an example of the surgeon console user interface in an application mode, according to certain aspects of the disclosure.

FIG. 5A shows an example UI 500A of the surgeon console user interface 112 when the surgeon console 104 switches to the application mode. In this example, four applications are displayed in the transient information regions 504A and 504B on the left and right side regions, respectively. In particular, an application 520A for displaying patient vitals and an application 520B for displaying the ultrasound video of the patient are displayed on the left side region. An application 520C for initiating a teleconference with another surgeon and an application 520D for enabling an ICG view of the surgical video 132 are displayed on the right side region. In the UI 500A, two icons 530A and 530B are shown next to the identifier of the robotic arms to indicate that the respective robotic arms are locked since the surgeon console 104 is in the application mode.

If more applications are available than that can be displayed in the side regions, the surgeon 102 can scroll or page through the applications to the one that he or she is interested in. For example, the surgeon 102 can activate both hand controllers to have the applications displayed in the transient information regions 308 to be replaced with a new set of applications. Alternatively, or additionally, upon activating the hand controllers, a new window listing all the available applications can be displayed. The surgeon 102 can select the applications of interest from the list so that these applications can be displayed in the transient information regions 308 of the side regions. Other operations or combinations of operations of the control devices 106 can be employed to page through the applications.

Figure 5B:
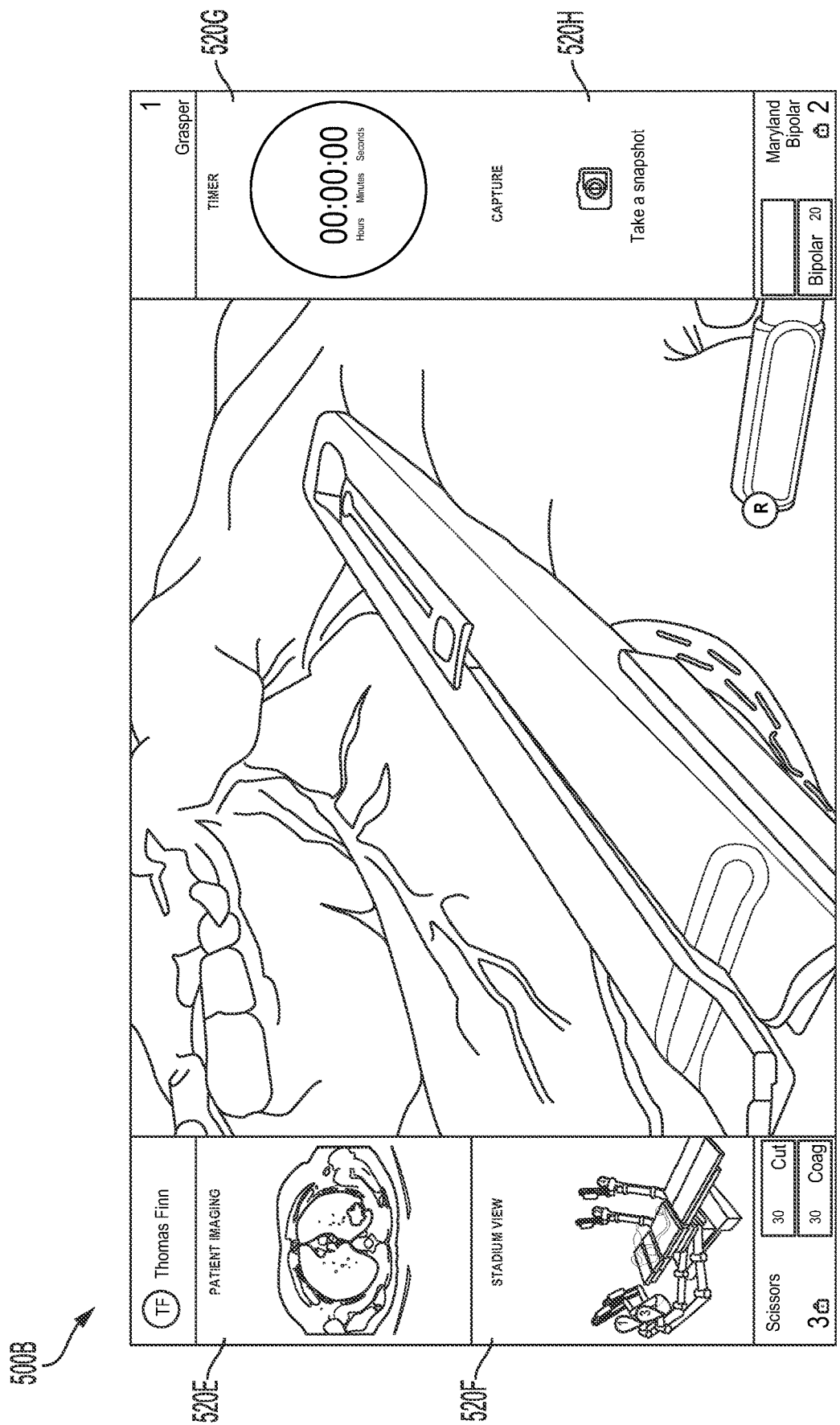
FIG. 5B shows another example of the surgeon console user interface in the application mode, according to certain aspects of the disclosure.

FIG. 5B shows an example UI 500B of the surgeon console user interface 112 after the surgeon console 104 requested a new set of applications. In the UI 500B, a second set of applications is shown. In particular, a patient imaging application 520E and a stadium view application 520F are shown on the left side region. A timer application 520G and a snapshot application 520H are shown on the right side region. If there are more applications available, the surgeon 102 can repeat the same actions to page through the rest applications.

As discussed above, the data shown in the applications displayed in the side regions are obtained from one or more external static or real-time data sources. For example, the auxiliary device 122 or the control system 120 communicates with a real-time data source for obtaining the patient vitals in real-time for the application 520A and an ultrasound probe for obtaining the ultrasound video for the application 520B. The auxiliary device 122 or the control system 120 further communicates with a patient imaging database, such as the database 140, to obtain the patient images for the application 520E. The auxiliary device 122 or the control system 120 can also communicate with a 3D model generator to obtain the 3D model of the robotic surgical device 114 for display in the stadium view application 520F. Other data sources may also be involved depending on the types of applications to be displayed in the surgeon console user interface 112.

By displaying the applications, the entirety of the transient information regions 308 on both side regions can be made interactive and thus are available for inputs in the application mode. In this case, the surgeon 102 can interact with the application to input a command to enable or disable the functionality of an application. For example, the surgeon 102 can move one of the hand controllers 208 to an application of interest and squeeze the hand controller 208 to enable the functionality and squeeze again to disable the functionality of the application, such as enabling or disabling the timer 520G or the ICG view application 520D. Other types of actions (e.g. tapping, rolling the hand controllers) or other types of control devices 106 (e.g. one or more of the pedals) can also be utilized to interact with the applications.

In some examples, the surgeon console user interface 112 can also be configured to allow the surgeon 102 to enlarge an application of interest. If the surgeon 102 selects to enlarge an application, the application is then presented in a full-screen mode, occupying the main region 302 or at least a portion thereof. A reduced-sized view of the surgical video 132 is maintained so that the surgeon 102 can still view the surgical video 132. If one of the applications is in an enlarged mode, the entire area occupied by the enlarged view becomes interactive and the surgeon 102 can use one or more of the control devices 106 to interact with the application.

Figure 5C:
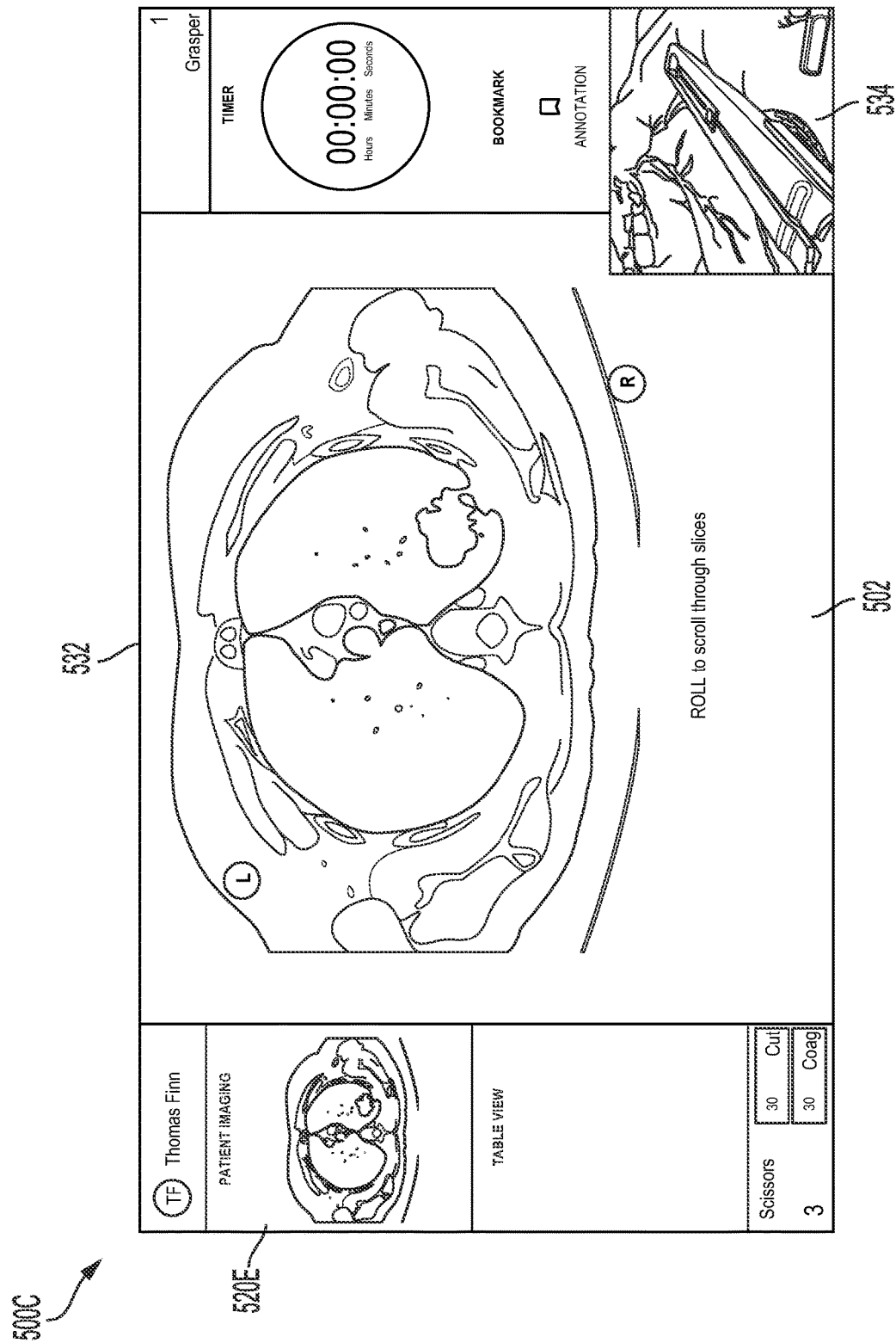
FIG. 5C shows another example of the surgeon console user interface in the application mode, according to certain aspects of the disclosure.

FIG. 5C shows an example UI 500C of the surgeon console user interface 112 when the surgeon console 104 requested to enlarge the view of the application 520E. As shown in this example, an enlarged version of the medial image 532 is shown in the entire area of the main region 502. The surgical video 132 is shown in a reduced-sized window 534 displayed in the top layer of the surgeon console user interface 112. In this view, the enlarged view of the application and the view of the surgical video 132 may block other regions of the surgeon console user interface 112, such as the persistent information region 510D and the transient information region 504B.

In the enlarged view of an application, the surgeon 102 can interact with the application. In the example of the patient imaging application 520E, the surgeon 102 can flip through the patient's images, such as by rolling a hand controller 208A or 208B. The surgeon 102 can further select one of the images by, for example, squeezing the hand controller. Further actions, such as rolling a hand controller, can be utilized to zoom in or out, or to flip through slices of the selected CT images. The surgeon console user interface 112 can exit the enlarged view of the application by moving the hand controller to the reduced-sized view 534 and selecting the view 534 through, for example, squeezing the hand controller.

Figure 5D:
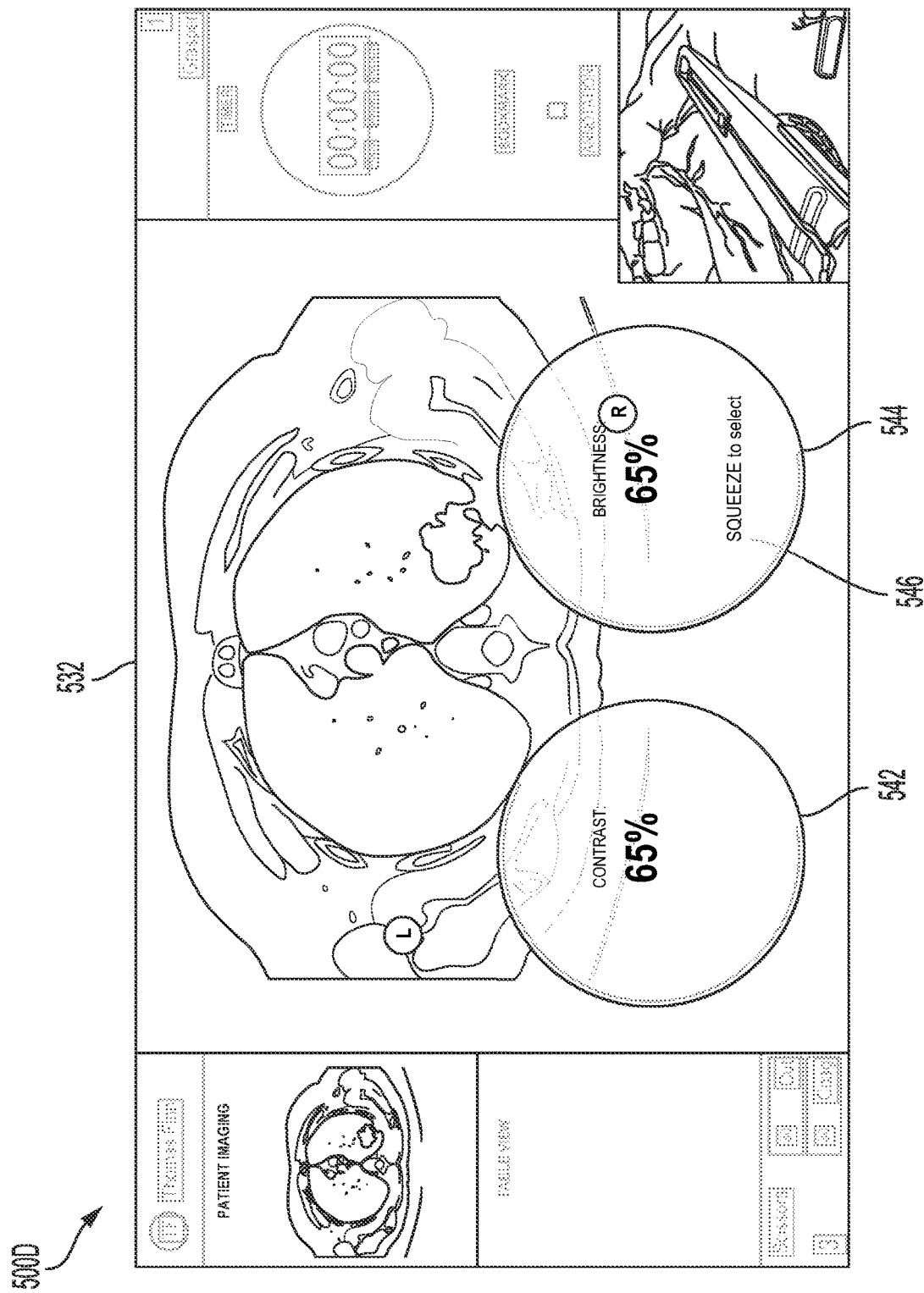
FIG. 5D shows another example of the surgeon console user interface in the application mode, according to certain aspects of the disclosure.

In other examples, the surgeon console user interface 112 may also display another user interface associated with an application by overlaying the user interface over the main region 302. FIG. 5D shows an example of the surgeon console user interface 112 with an image setting user interface overlaid over the main region 532. The image setting user interface shown in FIG. 5D includes a contrast setting component 542 for adjusting the contrast of the CT image shown in the main region 532 and a brightness setting component 544 for adjusting the brightness of the CT image. The surgeon 102 can make the adjustment by moving a hand controller to the corresponding component and roll the hand controller to reach a desired value of the parameter. The surgeon 102 further squeezes, taps or otherwise activates the hand controller to confirm the selection. In some implementations, a hint 546 is displayed in the surgeon console user interface 112 to remind the surgeon 102 about the operation used to make the adjustment.

As discussed above, as the surgeon console 104 exits the application mode, user interfaces of the applications 118 are removed from the surgeon console user interface 112. In some cases, however, information displayed in an application can be helpful to the surgeon 102 during the surgical procedure, such as the patient's medical image, patient vital information, etc. Thus, the surgeon 102 may want to keep this type of information even after the surgeon console 104 is switched to the surgery mode. To allow the surgeon 102 to access the information provided through the applications 118 after switching back to the surgery mode, the surgeon console user interface 112 is configured to allow the surgeon 102, while in the application mode, to pin or affix the user interface of an application to the surgeon console user interface 112.

Figure 5E:
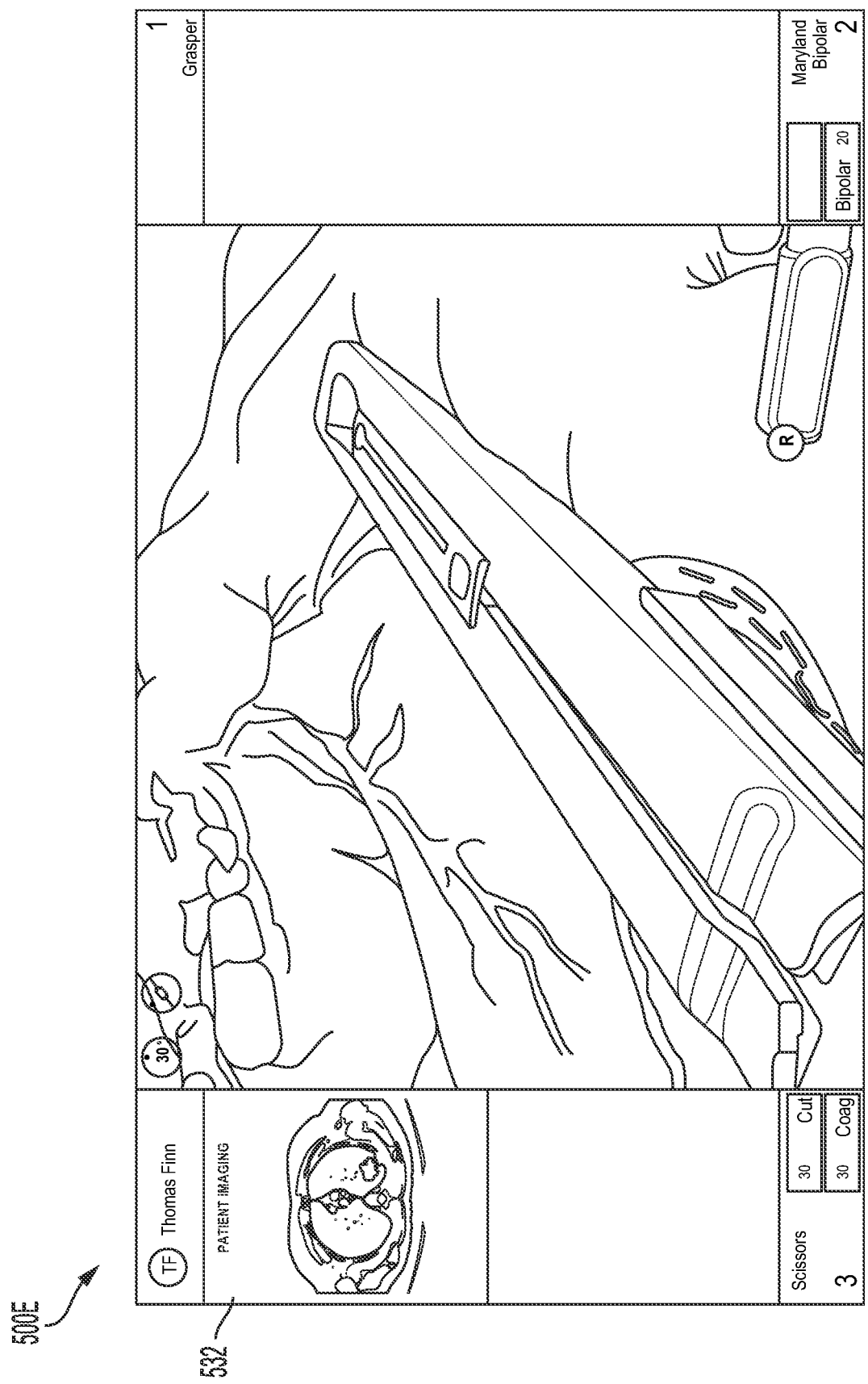
FIG. 5E shows another example of the surgeon console user interface in the application mode, according to certain aspects of the disclosure.

As a result, the pinned application user interface will remain in the surgeon console user interface 112 even after the surgeon console 104 switches to the surgery mode. To reduce the distractions to the surgeon 102, the pinned application user interface is rendered non-interactive and thus is only used to display information. FIG. 5E shows an example of the surgeon console user interface 112 in the surgery mode with a user interface 532 of the medical image application pinned to the left side region. The user interface 532 shows the medical image that the surgeon 102 was reviewing when the surgeon 102 requested the pinning operation in the application mode. In this way, the surgeon 102 can refer to the medical image of the patient during the surgical procedure. Other applications can also be pinned or affixed to the surgeon console user interface 112, such as the timer application, the stadium view application, and so on. According to some examples, the pinned applications can be removed from the surgeon console user interface 112 by re-entering the application mode and unpinning the application through certain operations using the control devices 106, such as squeezing and holding the hand controllers.

Figure 6A:
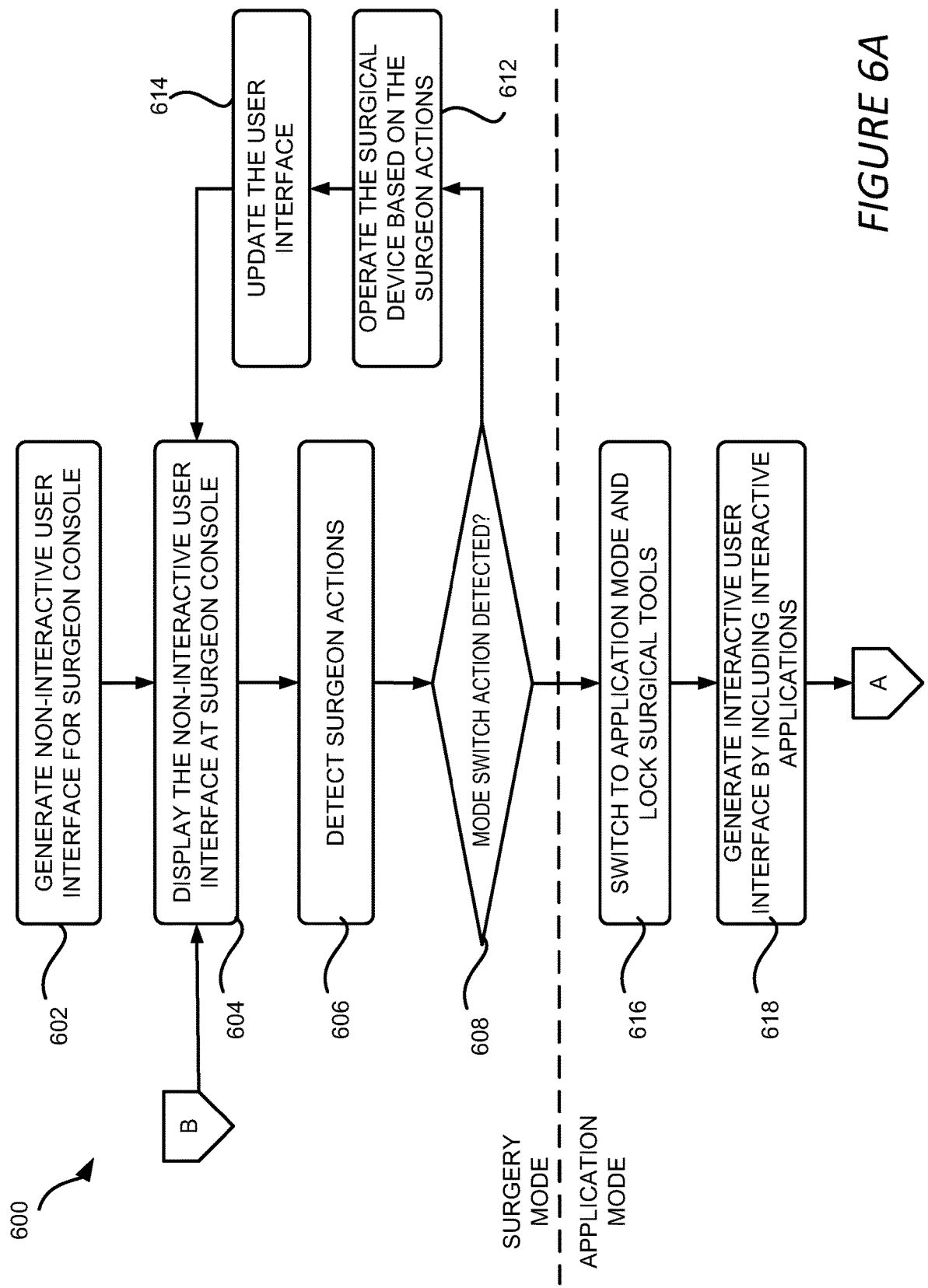

Referring now to FIGS. 6A and 6B, FIGS. 6A and 6B show an example method 600 for generating and presenting the surgeon console user interface 112 in a surgery mode and an application mode, according to certain aspects of the disclosure. The example method 600 will be discussed with respect to the example system 100 shown in FIG. 1, but may be employed according to any suitable system according to this disclosure.

At block 602, the surgeon console 104 operates in the surgery mode and the control system 120 generates a non-interactive surgeon console user interface 112 for the surgeon console 104. As discussed above in detail with respect to FIGS. 1-4D, in some examples, the surgeon console user interface 112 includes three areas: a main region and two side regions. The surgical video 132 of the operating site is displayed in the main region and other information related to the surgical procedure is displayed in the side regions, such as the status of the surgical tools and robotic arms, the status of the camera, and the surgeon information. In some examples, these types of information are displayed in persistent information regions on the side regions. Further, the status of the surgical tools and robotic arms controlled by a left controller or left pedals are displayed in the left side region, and the status of the surgical tools and robotic arms controlled by a right controller or right pedals are displayed in the right side region.

At block 604, the control system 120 transmits the surgeon console user interface 112 to the surgeon console 104 to have it displayed on the display device 108. At block 606, the control system 120 detects the actions performed by the surgeon 102. For example, the control system 120 detects the control devices 106 operated by the surgeon 102, including the hand controllers and various pedals.

At block 608, the control system 120 determines if the surgeon 102 has performed the mode switch actions that trigger the surgeon console 104 to switch from the surgery mode to the application mode. As discussed in detail above with respect to FIGS. 1 and 2, the mode switch action can include at least activation of a clutch device configured to lock the robotic arms and the associated surgical tools. In one example, the clutch device is a clutch pedal. The mode switch action may further include activation of one or more hand controllers, such as squeezing, tapping or rolling the one or more hand controllers. In another implementation, the mode switch action may include activating the clutch device along with another pedal. Various other combinations of actions can also be used as the mode switch actions.

If it is determined that the mode switch actions were not detected, the method 600 includes, at block 612, operating the robotic surgical device 114 based on the actions of the surgeon 102. The control system 120 passes the control signal sent by the surgeon 102 through the control devices 106 to the robotic surgical device 114 to control the surgical tools 126. At block 614, the control system 120, or more specifically, the UI generator 138, updates the surgeon console user interface 112 based on the current status of the robotic surgical device 114. For example, the control system 120 updates the status of the surgical tools and robotic arms shown in the surgeon console user interface 112. If the status of a surgical tool and a robotic arm reaches a state that requires the attention of the surgeon 102, the control system 120 generates and adds a warning message to the surgeon console user interface 112. Depending on how critical the message is, the warning message may be displayed in the side regions or overlaid over the main region. In some configurations, a non-critical message is displayed in a transient information region of a side region for a predetermined time period or when the condition causing the generation of the warning message no longer exists. A critical message is overlaid on top of the surgical video 132 and persistently displayed until the issue is resolved. The updated surgeon console user interface 112 is displayed at the surgeon console 104 at block 604.

If it is determined, at block 608, that the mode switch action is detected, the method 600 involves switching the surgeon console 104 to the application mode at block 616. The control system 120 further causes the robotic arms and surgical tools locked. At block 618, the control system 120 generates the surgeon console user interface 112 for the application mode by including interactive applications. As discussed above in detail with respect to FIGS. 3 and 5A-5E, the applications are displayed in the transient information regions of the side regions. Each of the transient information regions 308 may be configured to present no more than a maximum number of simultaneous applications, e.g. two applications, to reduce screen clutter and ensure enough screen space is provided to each application.

At block 620, the control system 120 sends the surgeon console user interface 112 to the surgeon console 104 for display. At block 624, the control system 120 detects the actions performed by the surgeon 102 using the control devices 106 in order to determine the operations to be performed on the surgeon console user interface 112. For example, squeezing a hand controller corresponds to a selection of a user interface control; rolling a hand controller corresponds to increasing or decreasing the value of a parameter; squeezing both hand controllers corresponds to pinning the user interface of an application to the surgeon console user interface 112; and so on.

At block 624, the control system 120 determines if the actions performed by the surgeon 102 matches the mode switch action. In some examples, when the surgeon console 104 is in the application mode, the mode switch action includes at least releasing the clutch device, such as the clutch pedal. Further actions, such as squeezing and holding both hand controllers may also be required in order to switch the surgeon console 104 from the application mode to the surgery mode. If the mode switch action is not detected at block 624, the control system 120 causes the application to be executed based on the surgeon's actions. At block 628, the control system 120 updates the surgeon console user interface 112 based on the execution of the application. For instance, if the surgeon 102 operates the control devices 106 to browse through the medical images of a patient, the surgeon console user interface 112 is updated to include the latest medical image that the surgeon 102 has requested. If the surgeon 102 has requested to turn on the ICG mode of the surgical video 132, the surgeon console user interface 112 is updated to show the ICG information on top of the surgical video 132.

If, at block 624, it is determined that the surgeon 102 has requested to exit the application mode by performing the mode switch action, the control system 120 causes the surgeon console 104 to exit the application mode. The control system 120 then passes the control signals generated by the surgeon 102 operating the control devices 106 to the robotic surgical device 114 to control the surgical tools 126. At block 630, the control system 120 updates the surgeon console user interface 112 by removing the user interfaces of the applications. In some scenarios where the surgeon 102 has requested to pin certain applications to the surgeon console user interface 112, the surgeon console user interface 112 will include the user interface of those applications. In any case, the surgeon console user interface 112 is rendered non-interactive to reduce the distraction to the surgeon 102 and to avoid misoperation. The updated surgeon console user interface 112 is then displayed on the surgeon console 104 at block 604 as described above.

It should be understood that while the above description focuses on using the hand controllers to interact with the applications presented in the surgeon console user interface 112, other control devices 106 or input devices, or combination thereof can also be utilized. For example, a combination of a pedal and one or more hand controller may be used to interact with the application. The touch screen of the display device 108, the touchpad of the surgeon console 104, or other types of input devices associated with the surgeon console 104 can also be utilized. In other examples, the applications in the surgeon console user interface 112 can also be interacted with through voice commands, alone or in combination with the control device as described above. Furthermore, although the above disclosure mainly describes using the action of squeezing the hand controller to select, confirm, or otherwise interact with the applications, other actions can also be employed, such as long or short tapping of the hand controller, various degrees of squeezing, or squeezing or tapping the hand controller for a certain period of time, and so on.

Figure 7:
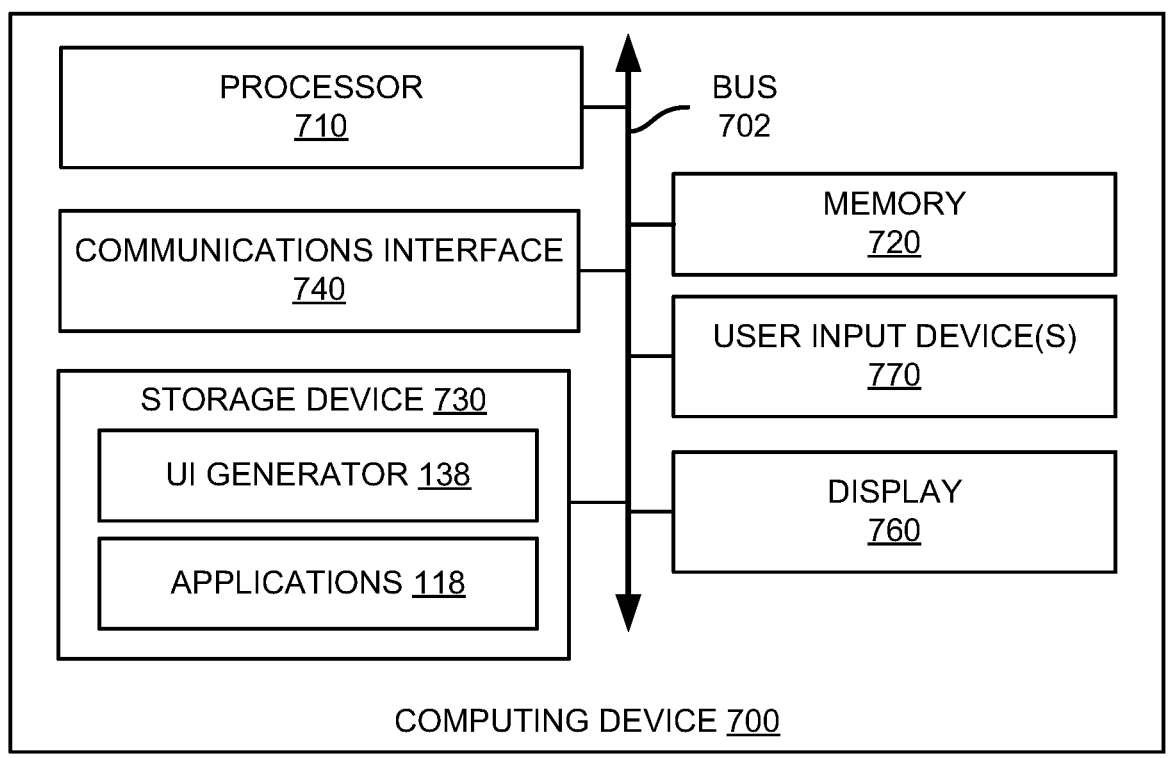
FIG. 7 shows an example computing device suitable for implementing aspects of the techniques and technologies presented herein.

Referring now to FIG. 7, FIG. 7 shows an example computing device 700 suitable for use in example systems or methods for improving the efficiency of robotic surgical procedures by integrating applications into the surgeon console user interface. The example computing device 700 includes a processor 710 which is in communication with the memory 720 and other components of the computing device 700 using one or more communications buses 702. The processor 710 is configured to execute processor-executable instructions stored in the memory 720 to generate the surgeon console user interface according to different examples, such as part or all of the example method 600 described above with respect to FIG. 6. The computing device, in this example, also includes one or more user input devices 770, such as a keyboard, mouse, touchscreen, microphone, etc., to accept user input. The computing device 700 also includes a display 760 to provide visual output to a user.

The computing device 700 can include or be connected to one or more storage devices 730 that provides non-volatile storage for the computing device 700. The storage devices 730 can store system or application programs and data utilized by the computing device 700, such as modules implementing the functionalities provided by the UI generator 138 and the applications 118. The storage devices 730 might also store other programs and data not specifically identified herein.

The computing device 700 also includes a communications interface 840. In some examples, the communications interface 740 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example non-transitory computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
    generating and displaying a surgeon console graphical user interface at a surgeon console associated with a robotic surgical device during a robotic surgical procedure, wherein
        the robotic surgical device comprises a plurality of surgical tools,
        the surgeon console comprises a plurality of control devices configured to control the plurality of surgical tools to perform the robotic surgical procedure,
        the plurality of control devices comprise a clutch device configured to, when activated, cause the plurality of surgical tools locked, and
        the surgeon console graphical user interface is configured to display information related to the robotic surgical procedure and is non-interactive;
    detecting a combination of user actions through the plurality of control devices, wherein the combination of user actions causes the surgeon console to operate in an application mode, and wherein the combination of user actions comprises activating the clutch device;
    in response to detecting the combination of the user actions,
        causing the plurality of surgical tools to be locked,
        modifying the surgeon console graphical user interface by including user interfaces of one or more applications and by configuring the surgeon console graphical user interface to be interactive,
        displaying the surgeon console graphical user interface at the surgeon console, and
        receiving a selection of a first application of the one or more applications to be affixed to the surgeon console graphical user interface;
    detecting a user action to exit the application mode, wherein the user action to exit the application mode comprises at least releasing the clutch device; and
    in response to detecting the user action to exit the application mode,
        causing the plurality of surgical tools to be unlocked, and
        updating the surgeon console graphical user interface by keeping the user interface of the first application in the surgeon console graphical user interface and removing a user interface of a second application of the one or more applications and by configuring the surgeon console graphical user interface to be non-interactive, wherein the first application and the second application are different, and
        displaying the surgeon console graphical user interface at the surgeon console.

2. The method of claim 1, wherein the clutch device is a clutch pedal, and wherein the combination of user actions comprises pressing the clutch pedal.

3. The method of claim 1, wherein the plurality of control devices comprise a left hand controller configured to control one or more surgical tools of the plurality of surgical tools, and a right hand controller configured to control remaining surgical tools of the plurality of surgical tools, and wherein the combination of user actions comprises activating the clutch device and activating at least one of the left hand controller or the right hand controller for at least a predetermined amount of time.

4. The method of claim 3, wherein at least one of the left hand controller or the right hand controller is used to interact with the modified surgeon console graphical user interface.

5. The method of claim 1, wherein the surgeon console graphical user interface comprises:
    a first region dedicated to displaying a video signal of the robotic surgical procedure captured by a camera of the robotic surgical device;
    a second region placed left to the first region and configured for displaying data related to one or more surgical tools of the plurality of surgical tools controlled by a left hand controller; and a third region placed right to the first region and configured for displaying data related to remaining surgical tools of the plurality of surgical tools controlled by a right hand controller.

6. The method of claim 5, wherein the user interfaces of the one or more applications are configured to be displayed in the second region or the third region.

7. A robotic surgical system comprising:
a robotic surgical device configured to control a plurality of surgical tools to perform a robotic surgical procedure;
a surgeon console configured to control the robotic surgical device, the surgeon console comprising a display device and a plurality of control devices configured to control the plurality of surgical tools to perform the robotic surgical procedure, wherein the plurality of control devices comprise a clutch device configured to, when activated, cause the plurality of surgical tools locked; and
a control device in communication with the robotic surgical device and the surgeon console, the control device comprising:
a processor; and
a non-transitory computer-readable medium having processor-executable instructions stored thereupon, which, when executed by the processor, cause the processor to:
generate and display a surgeon console graphical user interface on the display device of the surgeon console, the surgeon console graphical user interface configured to display information related to the robotic surgical procedure and is non-interactive;
detect a combination of user actions through the plurality of control devices, wherein the combination of user actions causes the surgeon console to operate in an application mode, wherein the combination of user actions comprises activating the clutch device;
in response to detecting the combination of the user actions, cause the plurality of surgical tools to be locked and modify the surgeon console graphical user interface by including user interfaces of one or more applications and by configuring the surgeon console graphical user interface to be interactive, display the surgeon console graphical user interface at the surgeon console, and receive a selection of a first application of the one or more applications to be affixed to the surgeon console graphical user interface;
detect a user action to exit the application mode, wherein the user action to exit the application mode comprises at least releasing the clutch device; and
in response to detecting the user action to exit the application mode, cause the plurality of surgical tools to be unlocked, and update the surgeon console graphical user interface by keeping the user interface of the first application in the surgeon console graphical user interface and removing a user interface of a second application of the one or more applications and by configuring the surgeon console graphical user interface to be non-interactive, wherein the first application and the second application are different, and display the surgeon console graphical user interface at the surgeon console.

8. The robotic surgical system of claim 7, wherein the clutch device is a clutch pedal, and wherein the combination of user actions comprises pressing the clutch pedal.

9. The robotic surgical system of claim 7, wherein the plurality of control devices comprise a left hand controller configured to control one or more surgical tools of the plurality of surgical tools, and a right hand controller configured to control remaining surgical tools of the plurality of surgical tools, and wherein the combination of user actions comprises activating the clutch device and activating at least one of the left hand controller or the right hand controller for at least a predetermined amount of time.

10. The robotic surgical system of claim 9, wherein at least one of the left hand controller or the right hand controller is used to interact with the modified surgeon console graphical user interface.

11. The robotic surgical system of claim 7, wherein the surgeon console graphical user interface comprises:
a first region dedicated to displaying a video signal of the robotic surgical procedure captured by a camera of the robotic surgical device;
a second region placed left to the first region and configured for displaying data related to one or more surgical tools of the plurality of surgical tools controlled by a left hand controller; and
a third region placed right to the first region and configured for displaying data related to remaining surgical tools of the plurality of surgical tools controlled by a right hand controller.

12. The robotic surgical system of claim 11, wherein the user interfaces of one or more applications are configured to be displayed in the second region or the third region.

13. The robotic surgical system of claim 12, wherein at least one of the user interfaces of one or more applications is interactive through at least one of the left hand controller or the right hand controller.

14. A non-transitory computer-readable medium comprising processor-executable instructions to cause a processor to:
generate and display a surgeon console graphical user interface at a surgeon console associated with a robotic surgical device during a robotic surgical procedure, wherein
the robotic surgical device comprises a plurality of surgical tools,
the surgeon console comprises a plurality of control devices configured to control the plurality of surgical tools to perform the robotic surgical procedure,
the plurality of control devices comprise a clutch device configured to, when activated, cause the plurality of surgical tools locked, and
the surgeon console graphical user interface is configured to display information related to the robotic surgical procedure and is non-interactive;
detect a combination of user actions through the plurality of control devices, wherein the combination of user actions causes the surgeon console to operate in an application mode, and wherein the combination of user actions comprises activating the clutch device;
in response to detecting the combination of the user actions,
cause the plurality of surgical tools to be locked,
modifying the surgeon console graphical user interface by including user interfaces of one or more applications and by configuring the surgeon console graphical user interface to be interactive, display the surgeon console graphical user interface at the surgeon console, and receive a selection of a first application of the one or more applications to be affixed to the surgeon console graphical user interface;

detect a user action to exit the application mode, wherein the user action to exit the application mode comprises at least releasing the clutch device; and in response to detecting the user action to exit the application mode, cause the plurality of surgical tools to be unlocked, and update the surgeon console graphical user interface by keeping the user interface of the first application in the surgeon console graphical user interface and removing a user interface of a second application of the one or more applications and by configuring the surgeon console graphical user interface to be non-interactive, wherein the first application and the second application are different, and display the surgeon console graphical user interface at the surgeon console.

15. The non-transitory computer-readable medium of claim 14, wherein the clutch device is a clutch pedal, and wherein the combination of user actions comprises pressing the clutch pedal.

16. The non-transitory computer-readable medium of claim 14, wherein the plurality of control devices comprise a left hand controller configured to control one or more surgical tools of the plurality of surgical tools, and a right hand controller configured to control remaining surgical tools of the plurality of surgical tools, and wherein the combination of user actions comprises activating the clutch device and activating at least one of the left hand controller or the right hand controller for at least a predetermined amount of time.

17. The non-transitory computer-readable medium of claim 16, wherein at least one of the left hand controller or the right hand controller is used to interact with the modified surgeon console graphical user interface.

18. The non-transitory computer-readable medium of claim 14, wherein the surgeon console graphical user interface comprises:

a first region dedicated to displaying a video signal of the robotic surgical procedure captured by a camera of the robotic surgical device;

a second region placed left to the first region and configured for displaying data related to one or more surgical tools of the plurality of surgical tools controlled by a left hand controller; and a third region placed right to the first region and configured for displaying data related to remaining surgical tools of the plurality of surgical tools controlled by a right hand controller.

19. The non-transitory computer-readable medium of claim 18, wherein the user interfaces of the one or more applications are configured to be displayed in the second region or the third region.

* * * * *